US008187831B2

(12) United States Patent
Yuan

(10) Patent No.: US 8,187,831 B2
(45) Date of Patent: May 29, 2012

(54) DETERMINATION OF IONS USING ION-SENSITIVE ENZYMES

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 120 days.

(21) Appl. No.: 10/665,883

(22) Filed: Sep. 19, 2003

(65) Prior Publication Data

US 2005/0142606 A1    Jun. 30, 2005

(51) Int. Cl.
  *C12Q 1/34* (2006.01)
  *C12N 9/14* (2006.01)
  *G01N 33/20* (2006.01)
(52) U.S. Cl. ......... 435/18; 530/350; 435/195; 435/69.7; 436/74; 436/79
(58) Field of Classification Search .................. None
See application file for complete search history.

(56) References Cited

U.S. PATENT DOCUMENTS

| 4,588,684 | A | 5/1986 | Brake ........................... 435/69.4 |
| 4,608,335 | A | 8/1986 | Fossati |
| 4,948,729 | A | 8/1990 | Piatak, Jr. et al. ............. 435/69.1 |
| 5,030,563 | A | 7/1991 | Schendel et al. ............. 435/69.8 |
| 5,171,670 | A | 12/1992 | Kronenberg et al. ........ 435/68.1 |
| 5,334,507 | A | 8/1994 | Soya et al. |
| 5,501,958 | A | 3/1996 | Berry et al. |
| 5,710,248 | A | 1/1998 | Grose ........................... 530/327 |
| 5,719,036 | A | 2/1998 | Tadano et al. |
| 5,885,811 | A | 3/1999 | Hansen ........................ 435/477 |
| 5,914,250 | A | 6/1999 | Hansen ........................ 435/69.1 |
| 6,194,200 | B1 | 2/2001 | Rose et al. .................. 435/320.1 |
| 7,022,494 | B2 | 4/2006 | Yuan |
| 2005/0069970 | A1 | 3/2005 | Yuan |
| 2005/0266508 | A1 | 12/2005 | Yuan |

FOREIGN PATENT DOCUMENTS

| EP | 0 121 352 | 10/1984 |
| EP | 0 186 643 | 7/1986 |
| EP | 0 196 864 | 10/1986 |
| EP | 0727495 | 8/1996 |
| JP | 6-311897 | 11/1994 |
| WO | WO 89/03886 | 5/1989 |
| WO | WO 00/28041 | 5/2000 |
| WO | WO-2005/017136 A1 | 2/2005 |

OTHER PUBLICATIONS

Lopez-Caronado, J.M., et al. (1999) J. Biol. Chem. 274(23), 16034-16039.*
Kurganov, R.I., et al. (2001) Anal. Chim. Acta 427, 11-19.*
Murguia, J.R., et al. (1995) Science 267, 232-234.*
Gil-Mascarell et al., Plant J., vol. 17, pp. 373-383, 1999.*
Ngo et al. in The Protein Folding Problem and Tertiary Structure Prediction, 1994, Merz et al. (ed.), Birkhauser, Boston, MA, pp. 433 and 492-495, Ref: U, Form-892.*
Bastin et al., Mol. Biochem. Parasitology 77:235-239 (1996).
Baykov et al., Anal. Biochem. 171:266-70 (1988).
Biochemistry 11:1726-1732 (1972).
Chen and Katz, BioTechniques 25(1):22-24 (1998).
Dichtl et al., EMBO J. 16(23):7184-95 (1997).
Gil-Mascarell et al., The Plant J. 17(4):373-83 (1999).
Gumber et al., Plant Physiol. 76:40-44 (1984).
Hardy and Randall, J. Cell. Sci. Suppl. 11:29-43 (1989).
Heppel and Hilmoe, J. Bio. Chem. 188:665-676 (1951).
Hobom et al., Dev. Biol. Stand. 84:255-62 (1995).
Kuhn et al., Mol. Gen. Genet. 167(3):235-41 (1979).
Murguia et al., J. Biol. Chem. 271(46):29029-33 (1996).
Murguia et al., Science 267:232-234 (1995).
Michiels et al., Trends Microbiol. 9(4):164-8 (2001).
Nagelkerken et al., Electrophoresis 18:2694-98 (1997).
Olah et al. Anal. Biochem. 221:94-102 (1994).
Peakman et al., Nucleic Acids Res. 20(22):6111-2 (1992).
Peng et al., J. Biol. Chem. 270(49):29105-10 (1995).
Prickett et al., BioTechniques 7(6):580-4 (1989).
Roesser and Yanofsky, Nucleic Acids Res. 19(4):795-800 (1991).
Rudiger et al., BioTechniques 23(1):96-97 (1997).
Saier et al., FASEB J. 2(3):199-208 (1988).
Shimojo et al., Clin. Chem. 35(9):1992-94 (1989).
Spiegelberg et al., J. Biol. Chem. 274(19):13619-28 (1999).
Tamaoku et al., Chem. Pharm. Bull. 30:2492-2497 (1982).
Tietz, Textbook of Clinical Chemistry, p. 1841, W.B. Saunders Co., Philadelphia (1986).
Tolbert and Lameh, J. Neurochem. 70:113-119 (1998).
Tseng and Verma, Gene 169:287-288 (1996).
Wang et al., Gene 169(1):53-58 (1996).
Watson et al., Molecular Biology of the Gene, 4th Ed., The Benjamin/Cummings Pub. Co., p. 224 (1987).
Xie et al., Endocrinology 139(11):4563-67 (1998).
Albert et al., J. Mol. Biol. (2000) 295:927-938.
International Search Report for PCT/US04/30522, mailed on Jul. 12, 2006, 4 pages.
Terpe, Appl. Microbiol. Biotechnol. (2003) 60:523-533.
Tzermia et al., Yeast (1997) 13:583-589.
Written Opinion of the International Searching Authority for PCT/US04/30522, mailed on Jul. 12, 2006.
International Preliminary Report on Patentability for PCT/US04/30522, mailed on Aug. 7, 2006.
Restriction Requirement from U.S. Appl. No. 10/665,888, mailed on Feb. 3, 2005.
Response to Restriction Requirement from U.S. Appl. No. 10/665,888, filed on Mar. 3, 2005.
Notice of Allowance from U.S. Appl. No. 10/665,888, mailed on Apr. 25, 2005.
Amendment After Allowance Under 37 C.F.R. § 1.312 from U.S. Appl. No. 10/665,888, filed Jul. 29, 2005.
Written Opinion of the International Searching Authority, from PCT/US04/30733, mailed on Aug. 26, 2005.
Response to the Written Opinion of the International Searching Authority, from PCT/US04/30733, filed on Nov. 28, 2005.
Office Action from EP 04 784 567.2-2404, mailed on Aug. 2, 2007.

(Continued)

*Primary Examiner* — Richard Hutson
(74) *Attorney, Agent, or Firm* — Morrison & Foerster LLP

(57) ABSTRACT

The invention relates generally to the field of sodium and lithium ion detection. In particular, the invention provides chimeric proteins, nucleic acids encoding chimeric proteins, methods and kits for assaying for sodium ions and for lithium ions in a sample, using inter alia, a 3'(2'),5'-bisphosphate nucleotidase.

40 Claims, 2 Drawing Sheets

OTHER PUBLICATIONS

Supplementary European Search Report for EP 04 784 567.2-2404, date mailed on Mar. 19, 2007, 4 pages.
Ankelo et al., Clinical Chemistry (2003) 49:908-915.
Bergmeyer et al., Methods of Enzymatic Analysis (Bergmeyer H.U. ed) $2^{nd}$ V.1, 505-507, Academic Press, Inc., New York NY (1974).
Bertocchi et al., Biosens. Bioelectron 11:1-10 (1996).
Bonucchi et al., Int. J. Artif. Organs 10:352-56 (1987).
Inouye et al., J. Biochem. 131:97-105 (2002).
Kimura, Ann. Clin. Biochem (1997) 34:384-388.
Lespinas et al., Clin. Chem. 35(4):654-58 (1989).
Naslund et al., Clin. Chem. 44(9):1964-73 (1998).
Reed et al., Clinical and Diagnostic Laboratory Immunology (2002) 9:1235-1239.
Roon et al., J. Biol. Chem. 247(13):4107-13 (1972).
Roon et al., Methods Enzymol. 17A:317-24 (1970).
Sumrada et al., J. Biol. Chem. 257(15):9119-27 (1982).
Tabata et al., J. Biolumin. Chemilumin. 2:63-67 (1988).
Non-Final Office Action from U.S. Appl. No. 11/191,691, mailed on Mar. 12, 2007.
Amendment in Response to Non-Final Office Action from U.S. Appl. No. 11/191,691, filed on Jul. 10, 2007.
Notice of Allowance and Examiner's Amendment from U.S. Appl. No. 11/191,691, mailed on Jul. 26, 2007.
Murguia et al., Journal of Biological Chemistry (1996) 271(46):29029-29033.
pBAD TOPO TA Expression Kit, Invitrogen Catalogue, Jan. 1, 2002, p. 75.
Supplementary European Search Report for EP 04784395.8, mailed Jun. 19, 2009, 6 pages.
Yenush et al., FEBS Letters (2000) 467(2-3):321-325.

* cited by examiner

DETERMINATION OF IONS USING ION-SENSITIVE ENZYMES

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 466992001100Seqlist.txt | Jun. 5, 2008 | 10,997 bytes |

BACKGROUND OF THE INVENTION

Serum electrolytes play a critical role in regulating normal physiologic functioning within and between cells. The testing of serum electrolytes is one of the most common analytical tests performed within hospitals. Such measurements are employed for routine monitoring of a patient as well as in emergency and life-threatening situations. Because of the vital role of electrolytes in normal physiologic responses, it is important that the measurement of the serum levels of electrolytes can be performed efficiently and accurately.

Sodium is one serum electrolyte critical in the physiologic control of water movement between the intracellular fluid compartment and the extracellular fluid compartment, i.e., maintaining osmotic pressure. In the healthy individual, the serum level of sodium is 135-145 mEq/l. Small deviations from normal level can have severe health consequences. An increased serum sodium can result from dehydration due to diarrhea or vomiting or nephrogenic diabetes. Low sodium levels usually are a result of too much water in the body, a condition associated with congestive heart failure, cirrhosis, nephritic syndrome, chronic renal failure, and syndrome of inappropriate anti-diuretic hormone (IADH).

Another source of electrolytes affecting physiologic function can also be those ions exogenously administered for therapeutic purposes. One example of such an ion is lithium. Therapeutic administration of lithium, typically as lithium carbonate, is one of the most effective agents for the treatment of patients suffering from bipolar disorder (manic depressive psychosis). Lithium acts by altering intraneuronal metabolism of catecholamines, inhibition of noradrenaline sensitive adenylate cyclase, and reduction in synaptic transmission and increase in neuronal excitability without modification of central nervous system (CNS) amine levels. Recently, studies have shown that lithium also holds promise in the treatment of Alzheimer's disease. However, lithium has severe toxic side effects. Toxicity is closely related to serum lithium levels and can occur at doses close to therapeutic levels, making the timely and accurate monitoring of serum levels critical. For example, serum $Li^+$ levels over 1.5 mM (12 hours after a dose) usually indicate a significant risk of lithium toxicity.

Currently, the two most commonly used methods to detect serum sodium and lithium are ion-selective electrode (ISE) and flame photometry. ISE relies on ion-specific electrodes. Ideally, each electrode possesses a unique ion-selective property that allows it to respond to the desired ion. However, in practice, interference from other ions in the sample compromise the specificity of the detecting electrode, rendering the electrodes susceptible to false readings. The instrumentation for ISE is relatively expensive, requires routine maintenance that is sometimes cumbersome and time-consuming, and demands that the operating technician to have a considerable degree of skill and knowledge for accurate and consistent readings. Flame photometry relies on the principle that certain atoms, when energized by heat, become excited and emit a light of characteristic wavelength of radiant energy when returning to ground state. The intensity of the characteristic wavelength of radiant energy produced by atoms in the flame is directly proportional to the number of atoms excited in the flames, which is directly proportional to the concentration of the substance of interest in the sample. Like ISE, the instrumentation required for this method is complex and relatively expensive. Moreover, flame photometry requires the use of combustible gas, introducing sometimes expensive hazard prevention measures.

Conventional methods to detect sodium and lithium ions in samples are limited by complex instrumentation, potentially expensive and cumbersome maintenance, additional hazards, and often time requirements not suitable to emergency situations. The present invention addresses these problems and is more user friendly in automated analyzers.

BRIEF SUMMARY OF THE INVENTION

In one aspect, the present invention is directed to an isolated chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase.

In another aspect, the present invention is directed to an isolated nucleic acid comprising a nucleotide sequence encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase. Recombinant cells comprising the nucleic acid and methods for producing the chimeric protein using the nucleic acid are also provided.

In still another aspect, the present invention is directed to a method for assaying for sodium ions in a sample, which method comprises: a) contacting the sample with a sodium-sensitive 3'(2'),5'-bisphosphate nucleotidase, wherein the nucleotidase consumes adenosine 3',5'-bisphosphate (PAP) and forms AMP and $P_i$; and b) assessing the consumption of PAP or the formation of AMP and $P_i$ in step a) to determine the presence or amount of sodium ions in the sample.

In yet another aspect, the present invention is directed to a method for assaying for sodium ions in a sample, which method comprises: a) contacting the sample with a first composition comprising adenosine 3',5'-bisphosphate (PAP); b) contacting the sample with a second composition comprising a sodium-sensitive 3'(2'),5'-bisphosphate nucleotidase; and c) assessing the production of AMP to determine the presence or amount of sodium ions in the sample. In one embodiment, the first composition further comprises 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, and the second composition further comprises adenosine deaminase, 5'-nucleotidase, and $MgCl_2$. Kits for assaying for sodium ions using the methods are also provided.

In still another aspect, the present invention is directed to a method for assaying for lithium ions in a sample, which method comprises: a) contacting the sample with a lithium-sensitive 3'(2'),5'-bisphosphate nucleotidase, wherein the nucleotidase consumes adenosine 3',5'-bisphosphate (PAP) and forms AMP and $P_i$; and b) assessing the amount of PAP consumed or AMP formed in step b) to determine the presence or absence of lithium ions in the sample. In one embodiment, the sample is first contacted with a sodium blocking agent. In a specific embodiment, the blocking agent is 3',5' bisphosphate nucleotidase.

In yet another aspect, the present invention is directed to a method for assaying for lithium ions in a sample, which method comprises: a) contacting the sample with a first composition comprising a adenosine 3',5'-bisphosphate (PAP); b) contacting the sample with a second composition comprising a lithium-sensitive 3'(2'),5'-bisphosphate nucleotidase; and c) assessing the production of a detectable product to determine the presence or absence of lithium ions in the sample. In one embodiment, the first composition further comprises 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, and the second composition further comprises adenosine deaminase, 5'-nucleotidase, and $MgCl_2$. In one embodiment, the sample is first contacted with a sodium blocking agent. In a preferred embodiment, the sodium blocking agent is 4,7,13,16,21-pentaoxa-1,10-diazabicyclo[8.8.5]-tricosane. Kits for assaying for lithium ions using the method are also provided.

DETAILED DESCRIPTION OF THE INVENTION

Figure 1:
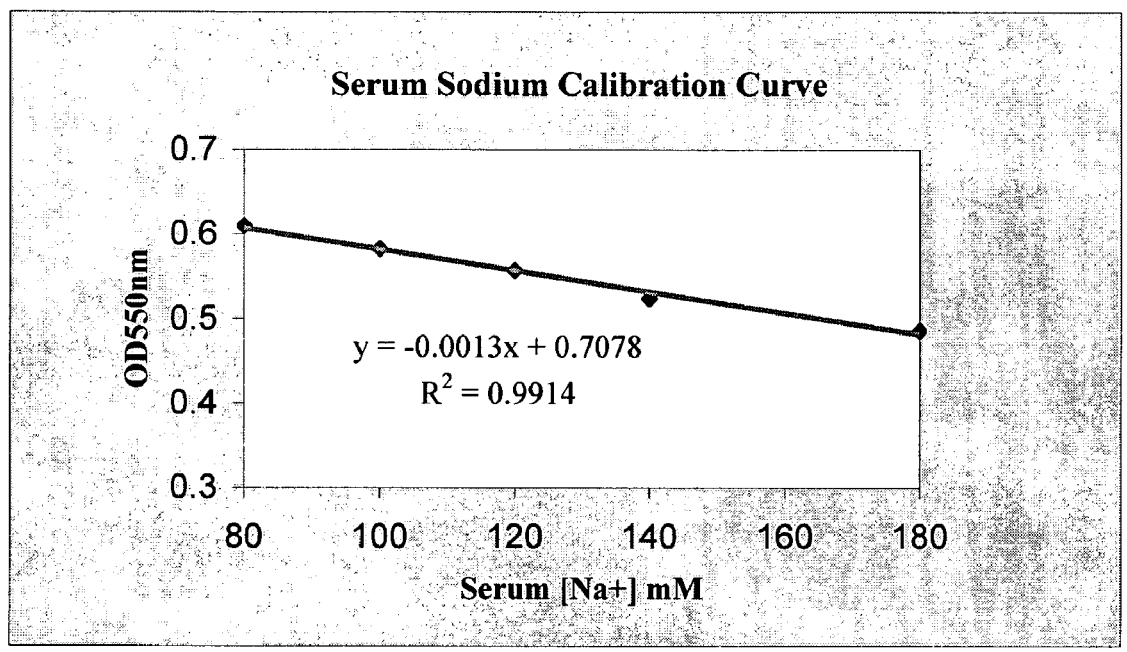
FIG. 1 is a serum sodium calibration curve. The calibration curve was generated using the methods disclosed in the Example 1. Briefly, the calibration curve was constructed by plotting the ΔA values of the standards against the corresponding sodium concentration.
Figure 2:
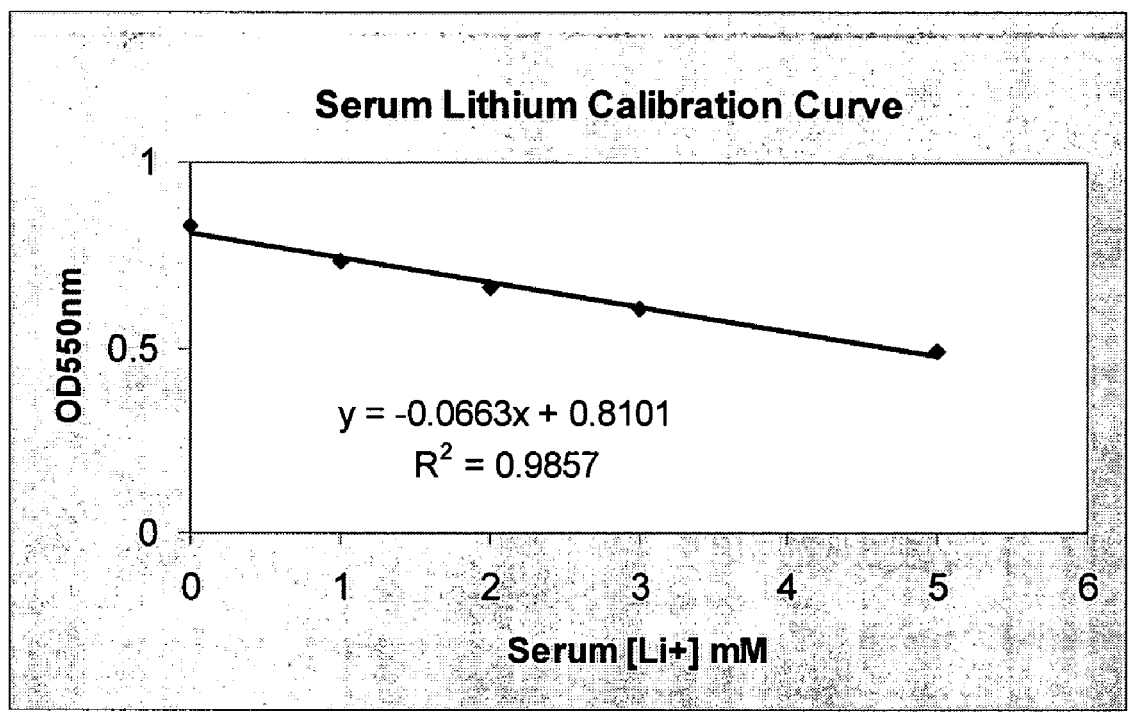
FIG. 2 is a serum lithium calibration curve. The calibration curve was generated using the methods disclosed in the Example 2. Briefly, the calibration curve was constructed by plotting the ΔA values of the standards against the corresponding lithium concentration.

For clarity of disclosure, and not by way of limitation, the detailed description of the invention is divided into the subsections that follow.
A. Definitions Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "leader sequence" refers to a peptide sequence, when fused to a target peptide or protein, increases stability and/or expression level of the target peptide or protein. Normally, a leader sequence increases stability and/or expression level of the target peptide or protein for at least 50%. Preferably, a leader sequence increases stability and/or expression level of the target peptide or protein for at least 1 fold, 2 folds, 5 folds, 10 folds or more than 10 folds. In the regulation of gene expression for enzymes concerned with amino acid synthesis in prokaryotes, the leader sequence codes for the leader peptide that contains several residues of the amino acid being regulated. Transcription is closely linked to translation, and if translation is retarded by limited supply of aminoacyl tRNA for the specific amino acid, the mode of transcription of the leader sequence permits full transcription of the operon genes; otherwise complete transcription of the leader sequence prematurely terminates transcription of the regulated gene.

As used herein, a "3'(2'),5'-bisphosphate nucleotidase" refers to an enzyme catalyzing the dephosphorylation of adenosine 3',5'-bisphosphate to yield corresponding adenosine 5'-phosphate (AMP) and $P_i$, as shown in the following reaction:

Other synonyms of 3'(2'),5'-bisphosphate nucleotidase include bisphosphate 3'-nucleotidase, HAL2 phosphatase, phosphoadenylate 3'-nucleotidase, 3'(2'),5'-bisphosphonucleoside, 3'(2')-phosphohydrolase, 3'-phosphoadenylylsulfate 3'-phosphatase, DPNPase, and PAP phosphatase. For purposes herein, the name "3'(2'),5'-bisphosphate nucleotidase" is used herein, although all such chemical synonyms are contemplated. "3'(2'),5'-bisphosphate nucleotidase" also encompasses a functional fragment or a derivative that still substantially retain its enzymatic activity catalyzing the dephosphorylation of adenosine 3',5'-bisphosphate to yield corresponding AMP and $P_i$. Typically, a functional fragment or derivative retains at least 50% of its 3'(2'),5'-bisphosphate nucleotidase activity. Preferably, a functional fragment or derivative retains at least 60%, 70%, 80%, 90%, 95%, 99% or 100% of its 3'(2'),5'-bisphosphate nucleotidase activity. It is also intended that a 3'(2'),5'-bisphosphate nucleotidase can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, 4th Edition, 1987, The Bejacmin/Cummings Pub. Co., p. 224). Such exemplary substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |

TABLE 1-continued

| Original residue | Conservative substitution |
| --- | --- |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may, be determined empirically or in accord with known conservative substitutions.

As used herein, a "composition" refers to any mixture of two or more products or compounds. It may be a solution, a suspension, liquid, powder, a paste, aqueous, non-aqueous, or any combination thereof.

As used herein, a "combination" refers to any association between two or among more items.

As used herein, "biological sample" refers to any sample from a biologic source, including but not limted to blood, plasma, and serum samples.

As used herein, "plasma" refers to the fluid, noncellular portion of the blood, distinguished from the serum obtained after coagulation.

As used herein, "serum" refers to the fluid portion of the blood obtained after removal of the fibrin clot and blood cells, distinguished from the plasma in circulating blood.

As used herein, "fluid" refers to any composition that can flow. Fluids thus encompass compositions that are in the form of semi-solids, pastes, solutions, aqueous mixtures, gels, lotions, creams, and other such compositions.

As used herein, "whole blood sample" refers to a blood sample containing both the cell and fluid portions of blood.

As used herein, "red blood cell sample" refers to the red blood cells portion of the blood obtained after removal of the serum portion of the blood.

As used herein, "peroxidase" refers to an enzyme that catalyzes a host of reactions in which hydrogen peroxide is a specific oxidizing agent and a wide range of substrates act as electron donors. It is intended to encompass a peroxidase with conservative amino acid substitutions that do not substantially alter its activity. The chief commercially available peroxidase is horseradish peroxidase.

As used herein, "5'-nucleotidase" refers to an enzyme that catalyzes the formation of adenosine and $P_i$ from adenosine 5'-phosphate (AMP). It is intended to encompass 5'-nucleotidase with conservative amino acid substitutions that do not substantially alter its activity.

As used herein, "adenosine deaminase" refers to an enzyme that catalyzes the formation of inosine and $NH_3$ from adenosine. It is intended to encompass any adenosine deaminase with conservative amino acid substitutions that do not substantially alter it activity.

As used herein, "purine nucleoside phosphorylase" or "PNP" refers to an enzyme that catalyzes the formation of hypoxanthine and ribose-1-phosphate (RIP) from inosine and $P_i$. It is intended to encompass purine nucleoside phosphorylase with conservative amino acid substitutions that do not substantially alter its activity.

As used herein, "xanthine oxidase" refers to an enzyme that catalyzes the conversion of hypoxanthine to uric acid and $H_2O_2$ in the presence of $H_2O$ and $O_2$. Other synonyms include xanthine:$O_2$ oxide reductase. It is intended to encompass xanthine oxidase with conservative amino acid substitutions that do not substantially alter its activity.

As used herein, the abbreviations for any protective groups, amino acids and other compounds are in accord with their common usage, recognized abbreviations, or the IUPAC-IUB Commission on Biochemical Nomenclature, unless otherwise indicated (see *Biochemistry* 11: 1726 (1972)).

B. Chimeric Proteins Comprising a 3'(2'),5'-Bisphosphate Nucleotidase and Nucleic Acids Encoding the Same In one aspect, the present invention is directed to isolated chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase.

Any suitable bacterial leader sequences can be used. As disclosed in U.S. Pat. No. 6,194,200, expression of the polypeptide of interest as a fused protein with a leader sequence from another gene has several advantages in addition to providing for stability. For example, the presence of the N-terminal amino acids provides a means for using general purification techniques for purification of any of a variety of polypeptides. For example, the N-terminal amino acids of the N-protein are predictably antigenic, and thus specific antibodies raised against the N-terminal amino acids of the N-protein may be used for the amino purification of the fusion proteins containing the N-terminus of the N-protein. Furthermore, the N-terminus of the N-protein has a high positive charge, which facilitates purification of the desired protein by ion-exchange chromatography, and the like.

The leader sequence can also be a hydrophobic amino acid sequence, which may additionally function as a signal sequence for secretion. See U.S. Pat. No. 6,194,200. A DNA sequence encoding the signal sequence is joined upstream from and in reading frame with the gene of interest. Typically, the signal sequence includes a cleavage site which is recognized by a signal sequence peptidase. Thus, positioning the polypeptide of interest directly after the signal sequence cleavage site will allow it to be specifically cleaved from the signal sequence and secreted as a mature polypeptide. Examples of hydrophobic amino acid sequences include the bacterial alkaline phosphatase signal sequence; the OMP-A, B, C, D, E or F signal sequences; the LPP signal sequence, β-lactamase signal sequence; and toxin signal sequences.

Other leader sequences which can be used include hydrophilic sequences, for example the N-terminal 41 amino acid residues from amphiregulin which may provide for modification of the function of the polypeptide of interest. See U.S. Pat. No. 6,194,200. In addition, a cytotoxic agent such as a toxin A-chain fragment, ricin A-chain, snake venom growth arresting peptide, or a targeting molecule such as a hormone or antibody can be coupled covalently with the leader sequence with in most cases minimal effect on the biological activity of the gene product of interest. As with the other leader sequences, a DNA sequence encoding the leader sequence is joined upstream from and in reading frame with the gene of interest.

Where the leader sequence is not a signal sequence or does not contain a convenient natural cleavage site, additional amino acids may be inserted between the gene of interest and the leader sequence to provide an enzymatic or chemical cleavage site for cleavage of the leader peptide, following purification of the fusion protein, to allow for subsequent purification of the mature polypeptide. See U.S. Pat. No. 6,194,200. For example, introduction of acid-labile aspartyl-proline linkages between the two segments of the fusion protein facilitates their separation at low pH. This method is not suitable if the desired polypeptide is acid-labile. The fusion protein may be cleaved with, for example, cyanogen bromide, which is specific for the carboxy side of methionine residues. Positioning a methionine between the leader sequence and the desired polypeptide would allow for release of the desired polypeptide. This method is not suitable when the desired polypeptide contains methionine residues.

Other bacterial leader sequences disclosed in the following patents, patent application and references can also be used: WO 00/28041 and WO 89/03886; U.S. Pat. Nos. 5,914,250, 5,885,811, 5,171,670, 5,030,563, 4,948,729 and 4,588,684; EP Patent Nos. EP 0,196,864, EP 0,186,643 and EP 0,121, 352; Michiels et al., *Trends Microbiol.*, 9(4): 164-8 (2001); Hobom et al., *Dev. Biol. Stand.*, 84: 255-62 (1995); Hardy and Randall, *J. Cell. Sci. Suppl.*, 11: 29-43 (1989); Saier et al., *FASEB J.*, 2(3): 199-208 (1988); and Peakman et al., *Nucleic Acids Res.*, 20(22): 6111-2 (1992). Preferably, the bacterial leader sequence is a leader sequence of an *E. coli.* protein, e.g., the *E. coli.* leader sequences disclosed in Roesser and Yanofsky, *Nucleic Acids Res.*, 19(4): 795-800 (1991); and Kuhn et al., *Mol. Gen. Genet.*, 167(3): 235-41 (1979). In one example, the leader sequence has at least 40% identity to the amino acid sequence set forth in SEQ ID NO: 1 (MGGSGD-DDDLAL), in which the percentage identity is determined over an amino acid sequence of identical size to the amino acid sequence set forth in SEQ ID NO: 1. Preferably, the leader sequence has at least 50%, 60%, 70%, 80%, 90%, 95%, 99% or 100% identity to the amino acid sequence set forth in SEQ ID NO: 1, in which the percentage identity is determined over an amino acid sequence of identical size to the amino acid sequence set forth in SEQ ID NO: 1. Also preferably, the leader sequence binds to an antibody that specifically binds to an amino acid sequence set forth in SEQ ID NO: 1. Still preferably, the leader sequence comprises the amino acid sequence set forth in SEQ ID NO: 1.

The first peptidyl fragment can have any suitable length. For example, the first peptidyl fragment comprises about 5, 6, 7, 8, 9, 10, 11, 12, 13, 14, 15, 16, 17, 18, 19, 20, 21, 22, 23, 24, 25, 26, 27, 28, 29 or 30 amino acid residues. Preferably, the first peptidyl fragment comprises about 20 amino acid residues.

Any suitable 3',5' bisphosphate nucleotidase can be used. In one example, the 3',5' bisphosphate nucleotidease is of *Saccharomyces cerevisaie* origin (See e.g., Murguia et al., *J. Biol. Chem.*, 271(46):29029-33 (1996)). This nucleotidase is also known as the HAL2 nucleotidase. Moreover, any suitable 3',5' bisphosphate nucleotidase catalyzing the reaction defined in Section B can be used in the present compositions and methods. The enzyme useful in the present compositions and methods is not limited those enzymes having only 3'(2'), 5'-bisphosphate nucleotidase activity. For example, the enzyme may have dual enzymatic activity, e.g., Tol-1. Homologues of the HAL2 phosphatase are also contemplated. Useful enzymes capable of catalyzing the above reaction include, but are not limited to BPntase (see, e.g., Spiegelberg et al., *J. Biol. Chem.* 274(19):13619-28 (1999)), HsPIP, RnPIP (see, e.g., López-Coronado, et al., *J. Biol. Chem.* 274(23):16034-39 (1999), and Tol-1 (see, e.g., Miyamoto, et al., *J. Bacteriol.* 182(13):3619-25 (2000)). Other useful 3'(2'),5'-bisphosphate nucleotidases, e.g., 3',5' bisphosphate nucleotidases are disclosed in Peng et al., *J. Biol. Chem.* 270(49):29105-10 (1995), Dichtl et al., *EMBO J.*, 16(23):7184-95 (1997), Gil-Mascarell et al., *The Plant J.* 17(4):373-83 (1999). A functional fragment or a derivative of a 3'(2'),5'-bisphosphate nucleotidase that still substantially retain its enzymatic activity catalyzing the dephosphorylation of adenosine 3',5'-bisphosphate to yield corresponding adenosine 5'-phosphate (AMP) and $P_i$ can also be used.

Normally, a functional fragment or a derivative of a 3',5-bisphosphate nucleotidase retain at least 50% of its enzymatic activity. Preferably, a functional fragment or a derivative of a 3'(2'),5'-bisphosphate nucleotidase retain at least 50%, 60%, 70%, 80%, 90%, 95%, 99% or 100% of its enzymatic activity.

The dephosphorylation of adenosine 3',5' bisphosphate (PAP) can be assessed by any suitable methods. For example, the dephosphorylation of adenosine 3',5' bisphosphate can be assessed by assessing consumption of the adenosine 3',5' bisphosphate in the dephosphorylation reaction or the formation of the AMP or $P_i$ in the reaction.

Assays for enzymatic activities of 3'(2'),5'-bisphosphate nucleotidases are known in the art (See e.g., Murguía et al., *J. Biol. Chem.*, 271(46): 29029-33 (1996)). Exemplary methods for phosphatase activity include determining the formation of inorganic phosphate (Pi) and AMP include calorimetric methods (See, e.g., Gumber et al., *Plant Physiol.*, 76: 40-44 (1984); Baykov et al., *Anal. Biochem.* 171: 266-70 (1988)) and radioactive-labeled substrates (See, e.g., Spiegelberg et al., *J. Biol. Chem.* 274(19): 13619-28 (1999); Peng et al., *J. Biol. Chem.* 270(49): 29105-29110 (1995)).

In another example, the 3'(2'),5'-bisphosphate nucleotidase has at least 40% identity to the amino acid sequence set forth in SEQ ID NO:2 (ALERELLVATQAVRKASLLTKRIQSE-VISHKDSTTITKNDNSPVTTGDYAAQTIIINAIKSNFP-DDKVVGEESSSGLSDAFVSGILNEIKANDEVYNKNY-KKDDFLFTNDQFPLKSLEDVRQIIDFGNYEGGRKGR-FWCLDPIDGTKGFLRGEQFAVCLALIVDGVVQLGCI-GCPNLVLSSYGAQDLKGHESFGYIFRAVRGLGAFYS-PSSDAESWTKIHVRHLKDTKDMITLEGVEKGHSSHD-EQTAIKNKLNISKSLHLDSQAKYCLLALGLADVYLR-LPIKLSYQEKIWDHAAGNVIVHEAGGIHTDAMEDVP-LDFGNGRTLATKGVIASSGPRELHDLVVSTSCDVIQS-RNA), in which the percentage of identity is determined over an amino acid sequence of identical size to the amino acid sequence set forth in SEQ ID NO:2.

The first and second peptidyl fragments can be linked via any suitable linkage. For example, the first and second peptidyl fragments can be linked via a cleavable linkage.

The isolated chimeric protein can further comprise, at its C-terminus, a third peptidyl fragment comprising a second bacterial leader sequence from about 5 to about 30 amino acid residues. Any suitable bacterial leader sequences, including the ones described above, can be used.

In one example, the second bacterial leader sequence is a leader sequence of an *E. coli.* protein. in another example, the second bacterial leader sequence has at least 40% identity to the amino acid sequence set forth in SEQ ID NO:3 (KGELEGLPIPNPLLRTG), in which the percentage identity is determined over an amino acid sequence of identical size to the amino acid sequence set forth in SEQ ID NO:3. Preferably, the second bacterial leader sequence has at least 50%, 60%, 70%, 80%, 90%, 95%, 99% or 100% identity to the amino acid sequence set forth in SEQ ID NO:4, in which the percentage identity is determined over an amino acid sequence of identical size to the amino acid sequence set forth in SEQ ID NO:4. Also preferably, the second bacterial leader sequence binds to an antibody that specifically binds to an amino acid sequence set forth in SEQ ID NO:3. Also preferably, the second bacterial leader sequence comprises the amino acid sequence set forth in SEQ ID NO:3.

The third peptidyl fragment can have any suitable length. For example, the third peptidyl fragment comprises about 5, 6, 7, 8, 9, 10, 11, 12, 13, 14, 15, 16, 17, 18, 19, 20, 21, 22, 23, 24, 25, 26, 27, 28, 29 or 30 amino acid residues. Preferably, the third peptidyl fragment comprises about 20 amino acid residues.

The isolated chimeric protein can further comprise, at its C-terminus, a third peptidyl fragment comprising a peptide tag. Any suitable tag can be used. For example, the tag can be FLAG, HA, HA1, c-Myc, 6-His, AU1, EE, T7, 4A6, ϵ, B, gE and Ty1 tag (See Table 2).

TABLE 2

Exemplary epitope tag systems

| Epitope | Peptide | SEQ ID | Antibody | Reference |
|---|---|---|---|---|
| FLAG | AspTyrLysAspAspAspLys | 11 | 4E11 | Prickett[1] |
| HA | TyrProTyrAspValProAspTyrAla | 12 | 12Ca5 | Xie[2] |
| HA1 | CysGlnAspLeuProGlyAsnAspAsnSerThr | 13 | mouse MAb | Nagelkerken[3] |
| c-Myc | GluGlnLysLeuIleSerGluGluAspLeu | 14 | 9E10 | Xie[2] |
| 6-His | HisHisHisHisHisHis | 15 | BAbCO* | |
| AU1 | AspThrTyrArgTyrIle | 16 | BAbCO | |
| EE | GluTyrMetProMetGlu | 17 | anti-EE | Tolbert[4] |
| T7 | AlaSerMetThrGlyGlyGlnGlnMetGlyArg | 18 | Invitrogen | Chen[5] |
| | | | | Tseng[6] |
| 4A6 | SerPheProGlnPheLysProGlnGluIle | 19 | 4A6 | Rudiger[7] |
| ε | LysGlyPheSerTyrPheGlyGluAspLeuMetPro | 20 | anti-PKCε | Olah[8] |
| B | GlnTyrProAlaLeuThr | 21 | D11, F10 | Wang[9] |
| gE | GlnArgGlnTyrGlyAspValPheLysGlyAsp | 22 | 3B3 | Grose[10] |
| Ty1 | GluValHisThrAsnGlnAspProLeuAsp | 23 | BB2, TYG5 | Bastin[11] |

[1]Prickett, et al., Bio Techniques, 7(6): 580-584 (1989)
[2]Xie, et al., Endocrinology, 139(11): 4563-4567 (1998)
[3]Nagelkerke, et al., Electrophoresis, 18: 2694-2698 (1997)
[4]Tolbert and Lameh, J. Neurochem., 70: 113-119 (1998)
[5]Chen and Katz, Bio Techniques, 25(1): 22-24 (1998)
[6]Tseng and Verma, Gene, 169: 287-288 (1996)
[7]Rudiger, et al., Bio Techniques, 23(1): 96-97 (1997)
[8]Olah, et al., Biochem., 221: 94-102 (1994)
[9]Wang, et al., Gene, 169(1): 53-58 (1996)
[10]Grose, U.S. Pat. No. 5,710,248
[11]Bastin, et al., Mol. Biochem. Parasitology, 77: 235-239 (1996)
Invitrogen, Sigma, Santa Cruz Biotech In an example, the isolated chimeric protein comprises the amino acid sequence set forth in SEQ ID NO: 4

(mggsgddddlalALERELLVATQAVRKASLLTKRIQSEVISHKDSTTITKNDNSPVTTG

DYAAQTIIINAIKSNFPDDKVVGEESSSGLSDAFVSGILNEIKANDEVYNKNYKKD

DFLFTNDQFPLKSLEDVRQIIDFGNYEGGRKGRFWCLDPIDGTKGFLRGEQFAVCL

ALIVDGVVQLGCIGCPNLVLSSYGAQDLKGHESFGYIFRAVRGLGAFYSPSSDAES

WTKIHVRHLKDTKDMITLEGVEKGHSSHDEQTAIKNKLNISKSLHLDSQAKYCLL

ALGLADVYLRLPIKLSYQEKIWDHAAGNVIVHEAGGIHTDAMEDVPLDFGNGRT

LATKGVIASSGPRELHDLVVSTSCDVIQSRNAkgeleglpipnpllrtghhhhhh).

In another aspect, the present invention is directed to an isolated nucleic acid comprising a nucleotide sequence encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase.

In one example, the isolated nucleic acid comprises a nucleotide sequence encoding the chimeric protein comprising the amino acid sequence set forth in SEQ ID NO:4. In another example, the isolated nucleic acid comprises a nucleotide sequence set forth in SEQ ID NO: 5

(atgggcggatccggtgatgacgatgacctcgcccttGCATTGGAAAGAGAATTATTGGTTGCAACT

CAAGCTGTACGAAAGGCGTCTTTATTGACTAAGAGAATTCAATCTGAAGTGAT

```
                       -continued
TTCTCACAAGGACTCCACTACTATTACCAAGAATGATAATTCTCCAGTAACCA

CAGGTGATTATGCTGCACAAACGATCATCATAAATGCTATCAAGAGCAATTTT

CCTGATGATAAGGTAGTTGGTGAAGAATCCTCATCAGGATTGAGCGACGCATT

CGTCTCAGGAATTTTAAACGAAATAAAAGCCAATGACGAAGTTTATAACAAG

AATTATAAAAGGATGATTTTCTGTTTACAAACGATCAGTTTCCGCTAAAATC

TTTGGAGGACGTCAGGCAAATCATCGATTTCGGCAATTACGAAGGTGGTAGAA

AAGGAAGATTTTGGTGTTTGGATCCTATTGACGGAACCAAGGGGTTTTTAAGA

GGTGAACAGTTTGCAGTATGTCTGGCCTTAATTGTGGACGGTGTTGTTCAGCTT

GGTTGTATTGGATGCCCCAACTTAGTTTTAAGTTCTTATGGGGCCCAAGATTTG

AAAGGCCATGAGTCATTTGGTTATATCTTTCGTGCTGTTAGAGGTTTAGGTGCC

TTCTATTCTCCATCTTCAGATGCAGAGTCATGGACCAAAATCCACGTTAGACA

CTTAAAAGACACTAAAGACATGATTACTTTAGAGGGAGTTGAAAAGGGACAC

TCCTCTCATGATGAACAAACTGCTATCAAAAACAAACTAAATATATCCAAATC

TTTGCACTTGGATTCTCAAGCCAAGTACTGTTTGTTAGCATTGGGCTTAGCAGA

CGTATATTTACGTCTGCCTATCAAACTTTCTTACCAAGAAAAGATCTGGGACC

ATGCTGCAGGCAACGTTATTGTCCATGAAGCTGGAGGTATCCATACAGATGCC

ATGGAAGATGTTCCTCTAGACTTCGGTAACGGTAGAACGCTAGCTACGAAGGG

AGTTATAGCGTCAAGTGGCCCACGCGAGTTACATGACTTGGTGGTGTCTACAT

CATGCGATGTCATTCAGTCAAGAAACGCCaagggcgagcttgaaggtttgcctatccctaaccctctc ctccgtaccggtcatcatcaccatcaccattga).
```

In still another example, the isolated nucleic acid comprising a nucleotide sequence complementary to the nucleotide sequence encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase.

In another example, a recombinant cell containing the nucleic acid, or a complementary strand thereof, encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase, is contemplated.

A method of producing a chimeric protein is also contemplated, which method comprising growing a recombinant cell containing the nucleic acid encoding a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising a 3'(2'),5'-bisphosphate nucleotidase, such that the encoded chimeric protein is expressed by the cell, and recovering the expressed chimeric protein. The product of the method is further contemplated.

The chimeric proteins and the nucleic acids encoding the chimeric proteins can be prepared by any suitable methods, e.g., chemical synthesis, recombinant production or a combination thereof (See e.g., CURRENT PROTOCOLS IN MOLECULAR BIOLOGY, Ausubel, et al. eds., John Wiley & Sons, Inc. (2000) and Sambrook, et al., MOLECULAR CLONING: A LABORATORY MANUAL, Cold Spring Harbor Laboratory press, (1989)).

C. Methods and Kits for Assaying for Sodium Ions Using a Chimeric Protein

In still another aspect, the present invention is directed to a method for assaying for sodium ions in a sample, which method comprises: a) contacting the sample with a sodium-sensitive 3'(2'),5'-bisphosphate nucleotidase, wherein the nucleotidase consumes adenosine 3',5'-bisphosphate (PAP) and forms AMP and $P_i$; and b) assessing the consumption of PAP or the formation of AMP and $P_i$ in step a) to determine the presence or amount of sodium ions in the sample.

In yet another aspect, the present invention is directed to a method for assaying for sodium ions in a sample, which method comprises: a) contacting the sample with a first composition comprising adenosine 3',5'-bisphosphate (PAP); b) contacting the sample with a second composition comprising a sodium-sensitive 3'(2'),5'-bisphosphate nucleotidase; and c) assessing the production of AMP to determine the presence or amount of sodium ions in the sample. In one embodiment, the first composition further comprises 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, and the second composition further comprises adenosine deaminase, 5'-nucleotidase, and $MgCl_2$.

The dephosphorylation of adenosine 3',5' bisphosphate (PAP) can be assessed by any suitable methods. For example, the dephosphorylation of adenosine 3',5' bisphosphate can be assessed by assessing consumption of the adenosine 3',5' bisphosphate in the dephosphorylation reaction or the formation of the AMP or $P_i$ in the reaction.

In one embodiment, the formation of AMP can be assessed using a combination of 5'-nucleotidase, adenosine deaminase, purine nucleoside phosphorylase, xanthine oxidase, and peroxidase. For example, the following series of coupled enzymatic reactions can result in the production of detectable quinone dye:

Reaction (I):

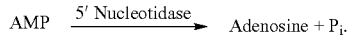
AMP $\xrightarrow{\text{5' Nucleotidase}}$ Adenosine + $P_i$.

Reaction (II):

Adenosine $\xrightarrow{\text{Adenosine Deaminase}}$ Inosine + $NH_3$.

Reaction (III):

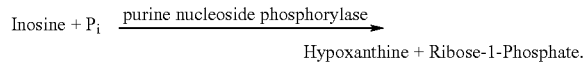
Inosine + $P_i$ $\xrightarrow{\text{purine nucleoside phosphorylase}}$ Hypoxanthine + Ribose-1-Phosphate.

Reaction (IV):

hypoxanthine + $2H_2O$ + $2O_2$ $\xrightarrow{\text{xanthine oxidase}}$ Uric acid + $2H_2O_2$.

Reaction (V):

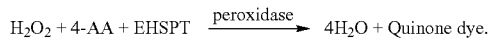
$H_2O_2$ + 4-AA + EHSPT $\xrightarrow{\text{peroxidase}}$ $4H_2O$ + Quinone dye.

Any suitable 3'(2'),5'-bisphosphate nucleotidease can be used. Any source or form known in the art that permits the production of $P_i$ and AMP from PAP is contemplated. In particular, any suitable chimeric proteins, including the ones described in the above Section B, can be used in the present methods. In one example, the chimeric protein comprises the amino acid sequence set forth in SEQ ID NO:4. In another example, the chimeric protein is encoded by the nucleotide sequence set forth in SEQ ID NO:5.

Any suitable adenosine 3',5'-bisphosphate (PAP) may be used. PAP may be isolated, purified or recombinantly generated from any source known in the art, that is subjec to the enzymatice activity of 3'(2'),5'-bisphosphate nucleotidase.

Any suitable 5'-nucleotidase, adenosine deaminase, purine nucleoside phosphorylase, and xanthine oxidase can be used. The enzymes can be derived from any source known in the art, including microbial and mammalian, that will permit the generation of a suitable detectable product. In one embodiment, ascorbate oxidase is also employed.

$H_2O_2$ formation can be assessed by any suitable means. In one embodiment, the $H_2O_2$ formation is assessed by a peroxidase and Trinder reaction. Any suitable peroxidase can be used. More preferably, a horseradish peroxidase is used. For example, the horseradish peroxidases with the following GenBank accession Nos. can be used: E01651; D90116 (prxC3 gene); D90115 (prxC2 gene); J05552 (Synthetic isoenzyme C(HRP-C)); S14268 (neutral); OPRHC (C1 precursor); S00627 (C1C precursor); JH0150 (C3 precursor); S00626 (C1B precursor); JH0149 (C2 precursor); CAA00083 (Armoracia rusticana); and AAA72223 (synthetic horseradish peroxidase isoenzyme C (HRP-C)). Any suitable Tinder reagent can be used herein. Hydrogen peroxide can quantitated by the quinone dye assay. See, e.g., Tamaoku, et al., *Chem. Pharm. Bull.* 30: 2497 (1982); Shimojo et al., *Clin. Chem.* 35(9):1992-94 (1989). The amount of quinine dye formed is inversely related to the amount of sodium ions in the sample.

Any suitable chromagen may be employed. In one embodiment, the chromagen is a Tinder reagent. Any suitable Tinder reagent can be used herein. In a specific embodiment, the chromagen is N-ethyl-N-(2-hydroxy-3-sulfopropyl)-3-m-toluidine (EHSPT) in combination with 4-aminoantipyrine (4-AA). Exemplary chromagens include, but are not limited to the combinations of a coupler (e.g., 4-aminoantipyrine, 3-methyl-2-benzothiazolinone hydrazone, NCP-04, NCP-05, NCP-06, or NCP-07) and a phenol derivative (e.g., phenol, 2-chlorophenol, 4-chlorophenol, 2,4-dichlorophenol) or an aniline derivative (e.g., aniline, N,N-dimeEhyl-m-anisidine, N-ethyl-N-(3-methyl-phenyl)-N'-acetylethylenediamine, N-ethyl-N-(.beta.-hydroxyethyl)-m-toluidine, N-ethyl-N-(hydroxy-3-sulfopropyl)-m-toluidine, N-ethyl-N-sulfopropyl-m-toluidine, N-ethyl-N-sulfopropyl-3,5-dimethoxyaniline, N-ethyl-N-(2-hydroxy-3-sulfopropyl)-3,5-dimethoxyaniline, N-ethyl-N-sulfopropyl-m-anisidine, N-ethyl-N-(3-methylphenyl)-N'-succinylethylenediamine, and N-ethyl-N-(2-hydroxy-3-sulfopropyl)-m-anisidine. Lueco dyes (e.g., 10-N-methylcarbamoyl-3,7-dimethylamino-10H-phenothiazine, bis[3-bis(4-chlorophenyl)methyl-dimethylaminophenyl]amine, 4,4-bis(dimethylamino) diphenyl(2,7-dihydroxy-1-naphthyl)methane) also are contemplated as useful in the present methods. Other aniline derivatives include N,N-bis(4-sulfobutyl)-3-methylaniline (TODB), N,N-bis(4-sulfobutyl)-3,5-dimethylaniline (MADB), N-ethyl-N-(2-hydroxy-3-sulfopropyl)-3,5-dimethylaniline (MAOS), N-2-hydroxy-3-sulfopropyl)-3,5-dimethyoxyaniline (HDAOS), N-(3-sulfopropyl)-3,5-dimethoxyaniline (HDAPS), N-ethyl-N-(3-sulfopropyl)-3-methoxyaniline (ADPS), and the like. Other suitable chromagens include N-(carboxymethylaminocarbonyl-4,4'-bis(dimethylamino)-diphenylamine (DA-64, E727 nm=9× $10^4$),10-(carboxymethylaminocarbonyl)-3,7-bis(dimethylamino)-phenothiazine (DA-67, E666 nm=9×$10^4$).

The sample can be contacted with the 3'(2'),5'-bisphosphate nucleotidase and peroxidase sequentially or simultaneously. Likewise, any other enzymes used can be contacted with the 3'(2'),5'-bisphosphate nucleotidase sequentially or simultaneously in a fashion that permits the formation of a detectable product.

If desirable, interference of the assay can be countered. For example, ascorbate interference can be countered using a copper (II) compound, a cholic acid or a bathophenanthroline disulphonic acid or a mixture thereof. Bilirubin interference can be countered using a ferrocyanide salt.

The present methods can be used to assay any suitable sample. Preferably, the sample is a biological sample. In one example, the sample is a blood sample, e.g., a plasma, serum, red blood cell or whole blood sample.

The present methods can be used for any suitable purpose. Preferably, the method is used in prognosis or diagnosis of a disease or disorder. In particular, the present methods are useful in assessing the presence or amount of sodium ions in a sample.

Any suitable conditions for detection or measurement of sodium ions can be used. The reaction temperature is usually in the range from 10° C. to 40° C., with a preferred temperature of 25° C. or 37° C. The reaction time is preferably not more than 15 minutes, most preferably about 10 minutes or less.

Any suitable means of performing calorimetric analysis can be used. In one embodiment, the samples are analyzed for the presence of quinone dye in a Roche Cobas Mira Chemistry Analyzer.

Any suitable means for preparing the sample may be employed. In one embodiment, serum or plasma samples are treated with heparinate.

In yet another aspect, the present invention is directed to a kit of assaying for sodium ions in a sample, which kit comprises: a) a first composition comprising a sodium-sensitive 3'(2'),5'-bisphosphate nucleotidase that consumes adenosine 3',5'-bisphosphate and forms AMP and $P_i$; and b) means for assessing the product formed or the substrate consumed by the nucleotidase to determine the presence or amount of the sodium ions in the sample. In one embodiment, the first composition further comprises adenosine deaminase, 5'-nucleotidase and $MgCl_2$. In one embodiment, the kit further comprises a second composition comprising 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, wherein the reaction of 4-AA and EHSPT in the presence of peroxidase is the means for assessing the product formed if sodium ions are not present. In some embodiments, the kit also comprises a low sodium serum standard and a high sodium serum standard. In a specific embodiment, the low sodium standard is 80 mM $Na^+$ and the high sodium standard is 180 mM $Na^+$.

Any suitable means can be included in the present kits. For example, the means for assessing dephosphorylation of the adenosine 3',5' bisphosphate by the chimeric protein can comprise a peroxidase. Preferably, the chimeric protein and the peroxidase are formulated in a single composition.

Any suitable 3'(2'),5'-bisphosphate nucleotidase, including the ones described in the above Sections B, can be used in the present methods. For example, the 3'(2'),5'-bisphosphate nucleotidase can comprise a chimeric protein, which chimeric protein comprises, from N-terminus to C-terminus: a) a first peptidyl fragment comprising a bacterial leader sequence from about 5 to about 30 amino acid residues; and b) a second peptidyl fragment comprising an 3'(2'),5'-bisphosphate nucleotidase. Preferably, the chimeric protein comprises the amino acid sequence set forth in SEQ ID NO:4. Also preferably, the chimeric protein is encoded by the nucleotide sequence set forth in SEQ ID NO:5.

The adenosine 3',5'-bisphosphate (PAP) to be used herein may be in any suitable form of a salt, so long as it contains no sodium ions. A preferred form is a potassium salt.

The compositions of the present invention may be formulated into a reagent having a pH adjusted by the addition of a buffer to pH 6 to 9. Any suitable buffer may be used. It is contemplated that such buffers contain no sodium ions. Exemplary buffers are Good's buffer, triethanolamine buffer, MES buffer, and tris buffer.

The compositions of the present invention may further contain any surfactant, preservative, stabilizer, and enzyme activator. Preferred examples of the surfactant are Triton-100. Preferred examples of the preservative include Thimerosal. Any suitable stabilizer can be used. In one embodiment, the stabilizer is a protein. In a specific embodiment, the protein is bovine serum albumin. Any suitable enzyme activator can be used. In one embodiment, the activator is $Mg^{2+}$ or a salt thereof, e.g., $MgCl_2$.

Any suitable concentration of 3'(2'),5'-bisphosphate nucleotidase can be used in a composition for measurement of sodium ions. In a preferred embodiment, the concentration is in the range of 0.1-5 u/ml, more preferably, 0.5-3 u/ml, most preferably 2-3 u/ml. Any suitable concentration of 5'-nucleotidase can be used. In a preferred embodiment, the concentration is in the range of 0.1-5 u/ml, more preferably, 0.5-3 u/ml, most preferably 2-3 u/ml. Any suitable concentration of adenosine deaminase can be used. In a preferred embodiment, the concentration is in the range of 0.1-5 u/ml, more preferably, 0.5-3 u/ml, most preferably 2-3 u/ml. Any suitable concentration of xanthine oxidase can be used. In a preferred embodiment, the concentration is in the range of 0.1-5 u/ml, more preferably, 0.5-3 u/ml, most preferably 1-2 u/ml. Any suitable concentration of peroxidase can be used. In a preferred embodiment, the concentration is in the range of 1-50 u/ml, more preferably, 5-30 u/ml, most preferably 5-10 u/ml. In one embodiment, ascorbate oxidase is employed.

The chromogen of the reduced type, N-ethyl-N-(2-hydroxy-3-sulfopropyl)-3-m-toluidine (EHSPT), and 4-aminoantipyrine (4-AA), or a salt thereof are used at any concentration suitable for measurement. The chromogen of the reduced type is preferably used at a concentration in the range of 0.01 to 10 mM. The N-ethyl-N-(2-hydroxy-3-sulfopropyl)-3-m-toluidine (EHSPT) or salt thereof is preferably used at a concentration of 4 mM. 4-aminoantipyrine (4-AA) or salt thereof is preferably used at a concentration of 2 mM.

In some embodiments, standards for calibration of the assay are included. In one embodiment, a low sodium serum standard and a high sodium standard are included. Preferably, the low sodium serum standard comprises 80-110 mM of sodium, preferably 80 mM, in serum and the high sodium serum standard comprises 160-180 mM of sodium, preferably 180 mM, in serum. In one embodiment, the presence or amount of sodium ions are calculated using a calibration curve. The amount of detectable chromagen is assessed at time 1 for a value of $A_1$ and at time 2 for a value of $A_2$. The resultant value is calculate in the following equation: $\Delta A = A_2 - A_1$. A calibration curve is generated by plotting the $\Delta A$ values of the standards. The amount of sodium in the samples are then determined by plotting the sample $\Delta A$ value on the calibration curve. In one embodiment, time 1 is 3 minutes after the addition of means to assess $P_i$ production and time 2 is 8 minutes after time 1.

D. Methods and Kits for Assaying for Lithium Ions Using a Chimeric Protein

In still another aspect, the present invention is directed to a method for assaying for lithium ions in a sample, which method comprises: a) contacting the sample with a lithium-sensitive 3'(2'),5'-bisphosphate nucleotidase, wherein the nucleotidase consumes adenosine 3',5'-bisphosphate (PAP) and forms AMP and $P_i$; and b) assessing the amount of PAP consumed or AMP formed in step b) to determine the presence or absence of lithium ions in the sample. In one embodiment, the sample is first contacted with a sodium blocking agent. In a specific embodiment, the sodium blocking agent is 4,7,13,16,21-pentaoxa-1,10-diazabicyclo[8.8.5]-tricosane.

In yet another aspect, the present invention is directed to a method for assaying for lithium ions in a sample, which method comprises: a) contacting the sample with a first composition comprising an adenosine 3',5'-bisphosphate (PAP); b) contacting the sample with a second composition comprising a lithium-sensitive 3'(2'),5'-bisphosphate nucleotidase; and c) assessing the production of a detectable product to determine the presence or absence of lithium ions in the sample. In one embodiment, the first composition further comprises 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, and, and the second composition further comprises adenosine deaminase, 5'-nucleotidase, and $MgCl_2$. In one embodiment, the sample is first contacted with a sodium blocking agent. In a specific embodiment, the sodium blocking agent is 4,7,13,16,21-pentaoxa-1,10-diazabicyclo[8.8.5]-tricosane.

Any suitable blocking agent may be used in the present methods. Exemplary blocking agents include, but are not limited to bis[(12-crown-4)methyl]-2-dodecyl-2-methylmalonate and 4,7,13,16,21-pentaoxa-1,10-diazabicyclo[8.8.5]- tricosane. In a preferred embodiment, the sodium blocking agent is 4,7,13,16,21-pentaoxa-1,10-diazabicyclo[8.8.5]-tricosane.

The dephosphorylation of adenosine 3',5' bisphosphate (PAP) can be assessed by any suitable methods. For example, the dephosphorylation of adenosine 3',5' bisphosphate can be assessed by assessing consumption of the adenosine 3',5' bisphosphate in the dephosphorylation reaction or the formation of the AMP or $P_i$ in the reaction.

Any suitable 3'(2'),5'-bisphosphate nucleotidease can be used, as disclosed in Section C. Any source or form known in the art that permits the production of $P_i$ and AMP from PAP is contemplated. In particular, any suitable chimeric proteins, including the ones described in the above Section B, can be used in the present methods. In one example, the chimeric protein comprises the amino acid sequence set forth in SEQ ID NO:4. In another example, the chimeric protein is encoded by the nucleotide sequence set forth in SEQ ID NO:5.

In one embodiment, the formation of AMP can be assessed using a combination of 5'-nucleotidase, adenosine deaminase, purine nucleoside phosphorylase, xanthine oxidase, and peroxidase. For example, the following series of coupled enzymatic reactions, as detailed in Section C, can result in the production of detectable quinone dye. In one embodiment, ascorbate oxidase is also employed.

Any suitable 5'-nucleotidase, adenosine deaminase, purine nucleoside phosphorylase, and xanthine oxidase can be used. The enzymes can be derived from any source known in the art, including microbial and mammalian, that will permit the generation of a detectable product if adenosine 3',5'-bisphosphate is consumed by the 3'(2'),5'-bisphosphate nucleotidase.

Any suitable means for assessing $H_2O_2$ formation may be employed as disclosed in Section C. Any suitable peroxidase can be used. More preferably, a horseradish peroxidase is used. Exemplary peroxidases, Trinder reagents, and other chromagens are those in Section C. In one embodiment, the amount of quinone dye formed is assessed to determine the presence or amount of $Li^+$ ions. Here, the amount of quinine dye formed is inversely related to the amount of lithium ions in the sample.

Any suitable means for preparing the sample may be employed. In one embodiment, serum or plasma samples are treated with heparinate.

The sample can be contacted with the 3'(2'),5'-bisphosphate nucleotidase and the peroxidase sequentially or simultaneously. Likewise, any other enzymes used can be contacted with the 3'(2'),5'-bisphosphate nucleotidase sequentially or simultaneously in a fashion that permits the formation of a suitable detectable product.

Any suitable conditions for detection or measurement of sodium ions can be used. The reaction temperature is usually in the range from 10° C. to 40° C., with a preferred temperature of 37° C. The reaction time is preferably not more than 15 minutes, most preferably about 9 minutes or less.

Any suitable means of performing colorimetric analysis can be used. In one embodiment, the samples are analyzed for the presence of quinone dye in a Roche Cobas Mira Chemistry Analyzer.

If desirable, interference of the assay can be countered. For example, ascorbate interference can be countered using a copper (II) compound, a cholic acid or a bathophenanthroline disulphonic acid or a mixture thereof. Bilirubin interference can be countered using a ferrocyanide salt.

The present methods can be used to assay any suitable sample. Preferably, the sample is a biological sample. In one example, the sample is a blood sample, e.g., a plasma, serum, red blood cell or whole blood sample.

Any suitable chimeric proteins, including the ones described in the above Section B, can be used in the present methods. In one example, the chimeric protein comprises the amino acid sequence set forth in SEQ ID NO:4. In another example, the chimeric protein is encoded by the nucleotide sequence set forth in SEQ ID NO:5.

The present methods can be used for any suitable purpose. Preferably, the method used in the prognosis or diagnosis of a disease or disorder. In one embodiment, the present methods are used to detect the presence or amount of lithium ions in a serum sample.

In one aspect, the present invention is directed to a kit for assaying for lithium ion in a sample, which kit comprises: a) a first composition comprising a lithium-sensitive 3'(2'),5'-bisphosphate nucleotidase; and b) a means for assessing the adenosine 3',5'-bisphosphate consumed or the AMP formed by the 3'(2'),5'-bisphosphate nucleotidase to determine the presence or amount of said lithium ions in the sample. In one embodiment, the kit further comprises a sodium blocking agent. In one embodiment, the first composition further comprises adenosine deaminase, 5'-nucleotidase and $MgCl_2$. In one embodiment, the kit further comprising a second composition comprising 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, wherein the reaction of 4-AA and EHSPT in the presence of peroxidase is the means for assessing the product formed if lithium ions are not present. The kit can also further comprises a low lithium serum standard, a medium lithium standard, and a high lithium serum standard.

Any suitable blocking agent may be used in the present methods. In a preferred embodiment, the sodium blocking agent is 4,7,13,16,21-pentaoxa-1,10-diazabicyclo[8.8.5]-tricosane.

The adenosine 3',5'-bisphosphate (PAP) to be used herein may be in any suitable form of a salt, so long as it contains no lithium ions. A preferred form is potassium salt.

The compositions of the present invention may be formulated into a reagent having a pH adjusted by the addition of a buffer to pH 6 to 9. Any suitable buffer may be used. It is contemplated that such buffers contain no sodium ions. Exemplary buffers are Good's buffer, 2-[N-morpholino] ethane-sulfonic acid (MES) buffer, and tris buffer.

The compositions of the present invention may further contain any surfactant, preservative, stabilizer, and enzyme activator. Preferred examples of the surfactant are Triton-100. Preferred examples of the preservative include Thimerosal. Any suitable stabilizer can be used. In one embodiment, the stabilizer is a protein. In a specific embodiment, the protein is bovine serum albumin. Any suitable enzyme activator can be used. In one embodiment, the activator is $Mg^{2+}$ or a salt thereof, e.g., $MgCl_2$.

Any suitable concentration of 3'(2'),(5')-bisphosphate nucleotidase can be used in a composition for measurement of sodium ions. In a preferred embodiment, the concentration is in the range of 0.1-5 u/ml, more preferably, 0.5-3 u/ml, most preferably 2-3 u/ml. Any suitable concentration of 5'-nucleotidase can be used. In a preferred embodiment, the concentration is in the range of 0.1-5 u/ml, more preferably, 0.5-3 u/ml, most preferably 2-3 u/ml. Any suitable concentration of adenosine deaminase can be used. In a preferred embodiment, the concentration is in the range of 0.1-5 u/ml, more preferably, 0.5-3 u/ml, most preferably 2-3 u/ml. Any suitable concentration of xanthine oxidase can be used. In a preferred embodiment, the concentration is in the range of 0.1-5 u/ml, more preferably, 0.5-3 u/ml, most preferably 2-3 u/ml. Any suitable concentration of peroxidase can be used. In a preferred embodiment, the concentration is in the range of 1-50 u/ml, more preferably, 1-30 u/ml, most preferably 5-10 u/ml.

Any suitable chromagen may be employes, particularly those in Section C. The chromagen of the reduced type, N-ethyl-N-(2-hydroxy-3-sulfopropyl)-3-m-toluidine (EH- SPT), and 4-aminoantipyrine (4-AA), or a salt thereof are used at any concentration suitable for measurement. The chromagen of the reduced type is preferably used at a concentration in the range of 0.01 to 10 mM. The N-ethyl-N-(2-hydroxy-3-sulfopropyl)-3-m-toluidine (EHSPT) or salt thereof is preferably used at a concentration of 4 mM. 4-aminoantipyrine (4-AA) or salt thereof is preferably used at a concentration of 2 mM.

In some embodiments, standards for calibration of the assay are included. In one embodiment, a low lithium serum standard, a medium lithium standard, and a high lithium standard are included. Preferably, the low lithium serum standard comprises 0 mM of lithium in serum, and the medium lithium serum standard comprises 0.5-1.5 mM of lithium in serum, preferrably 1 mM, and the high lithium serum standard comprises 2.5-3.5 mM of lithium, preferrably 3.0 mM, in serum. In one embodiment, the presence or amount of lithium ions are calculated using a calibration curve. The amount of detectable chromagen is assessed at time 1 for a value of $A_1$ and at time 2 for a value of $A_2$. The resultant value is calculate in the following equation: $\Delta A = A_2 - A_1$. A calibration curve is generated by plotting the $\Delta A$ values of the standards. The amount of lithium in the samples are then determined by plotting the sample $\Delta A$ value on the calibration curve. In one embodiment, time 1 is 6 minutes after the addition of means to assess $P_i$ production and time 2 is 3 minutes after time 1.

E. Examples

Example 1

Sodium Ion Detection Assay Kit

Intended Use. The exemplary assay kit is for the quantitative in vitro determination of sodium in serum and plasma.

Assay Principle. Sodium was determined spectrophotometrically through a kinetic coupling assay system involving the chimeric 3'(2'),5'-bisphosphate nucleotidase (as described in Section B) whose activity was sensitive to sodium concentration ($IC_{50}$=20 mM). Through enzymatic coupling, the phosphatase substrate, adenosine 3',5'-bisphosphate (PAP) was converted to hypoxanthine by a series of enzymatic reactions to generate uric acid and hydrogen peroxide ($H_2O_2$). $H_2O_2$ generated reacts with N-Ethyl-N-(2-hydroxy-3-sulfopropyl)-3-m-toluidine (EHSPT) and 4-aminoantipyrine (4-AA) in the presence of peroxidase (POD) to form a quinone dye which had maximal absorbance at 556 nm. The rate of the quinine dye formation was inversely proportion to the concentration of sodium in serum samples. The enzymatic coupling reaction scheme is shown below in Table 3:

Key Assay Characteristics. The sodium enzymatic assay was a two reagent (R1 and R2) based kinetic assay system. The results were obtained in 10 min by measuring absorbance at 550 nm. No off line pretreatment was needed. The assay had a wide measuring range from 80 to 180 mmol/L. The assay offered excellent precision as shown in the table below:

TABLE 4

|  | 130M $Na^+$ | 150 mM $Na^+$ |
|---|---|---|
| Intra-assay | CV % = 3.8% | CV % = 4.8% |
| Inter-assay | CV % = 4.2% | CV % = 4.1% |

TABLE 5

| Reagents |
|---|
| Reagent 1. Buffer/enzyme/substrates |
|    Enzyme/substrate lyophilized powder containing |
|    Good's buffer, PAP, $MgCl_2$, 4-AA, Enzymes and stabilizers |
| Reagent 2. Buffer/protein/substrate |
|    Enzyme/substrate lyophilized powder containing |
|    Good's buffer, Enzymes, $MgCl_2$, and stabilizers |
| Low sodium Serum Standard |
| High sodium Serum Standard |

Reagent Preparation. One vial of Reagent 1 (R1) was reconstituted with 50 ml distilled water. The reagents were mixed gently by inversion and then allowed to stand a minimum of 10 min in an ice bath before use. The reconstituted R1 solution was stable for 1 week at 2-8° C. One vial of Reagent 2 (R2) was reconstituted with 25 ml of distilled water. The reagents were gently by inversion and then allowed to stand a minimum of 10 min in an ice bath before use. The reconstituted R2 solution was stable for 1 week at 2-8° C. Standards included were ready to use and were stable up to expiration date when stored under 2-8° C.

Normal Values. The normal Na+ values in serum are 136-146 mM (313-336 mg/dL).

Test samples. Test samples were serum or plasma treated with heparinate.

Assay Procedure.

1. Reconstituted R1 and R2 reagents as described in Reagent Preparation section and kept the reconstituted R1 and R2 reagents on ice bath.

TABLE 3

$$PAP + H_2O \xrightarrow{\text{Phosphatase}} AMP + P_i$$

$$AMP \xrightarrow{\text{5'-Nucleotidase/ADA deaminase/PNP}} Hypoxanthine + P_i + NH_3 + R\text{-}1\text{-}P$$

$$Hypoxanthine + 2H_2O + 2O_2 \xrightarrow{\text{Xanthine Oxidase}} Uric\ Acid + 2H_2O_2$$

$$H_2O_2 + 4\text{-}AA + EHSPT \xrightarrow{\text{Peroxidase}} 4H_2O + \text{Quinone dye} (\lambda\ max\ 556\ nm)$$

PAP: 3'-phophoadenosine 5'-phosphate (adenosine 3', 5'-bisphosphate)
AMP: Adenosine-5'-phosphate
PNP: Purine Nucleoside Phosphorylase
4-AA: 4-Aminoantipyrine
EHSPT: N-Ethyl-N-(2-Hydroxy-3-Sulfopropyl)-m-Toluidine 2. In a cuvette, mixed 180 μL of Reagent R1 and 20 μL of serum sample and incubated at 37° C. for 1 minute and then added 85 μL of Reagent 2.

3. Read absorbance (550 nm) at 3 min (2 min after addition of Reagent 2) as $A_1$. Incubated for a further 7 min and read the absorbance at 10 min as $A_2$.

4. Calculated $\Delta A = A_2 - A_1$

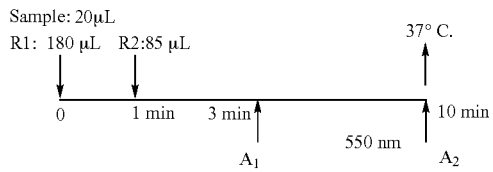

Calibration. This assay was calibrated daily using the enclosed low and high sodium standards. A calibration curve was constructed by plotting the ΔA values of the standards against the corresponding sodium concentrations. The sodium concentration of the sample was read from the calibration curve. A representative calibration curve is shown in FIG. 1.

Interference. The assay was not interfered by the following substances at indicated concentrations: $NH_4Cl$ at 0.5 mM; KPi at 1.5 mM; $CaCl_2$ at 5 mM; NaCl at 200 mM; KCl at 10 mM; $CuCl_2$ at 0.25 mM; $FeCl_3$ at 0.25 mM; $ZnCl_2$ at 0.25 mM; triglyceride at 250 mg/dl; ascorbic acid at 5 mM; and bilirubin at 10 mg/dl.

REFERENCES

1. N. Tietz. TEXTBOOK OF CLINICAL CHEMISTRY, p. 1841. W.B. Sauders Company, Philadelphia (1986)
2. L. Heppel and R. Hilmoe. *J. Bio. Chem.* 188, 665-676 (1951)
3. J. Murguia, J. Belles, and R. Serrano. *Science* 267, 232-234 (1995)

Example 2

Lithium Ion Detection Assay

Intended Use. The exemplary assay kit was for the quantitative in vitro determination of lithium in serum and plasma.

Assay Principle. Lithium was determined spectrophotometrically through a kinetic coupling assay system involving the chimeric 3'(2'),5'-bisphosphate nucleotidase, as described in Section B, whose activity was sensitive to lithium concentration ($IC_{50}$=0.1 mM). Through enzymatic coupling, the phosphatase substrate, adenosine 3',5'-bisphosphate (PAP) was converted to hypoxanthine by a series of enzymatic reactions to generate uric acid and hydrogen peroxide ($H_2O_2$). The $H_2O_2$ generated reacted with N-Ethyl-N-(2-hydroxy-3-sulfopropyl)-3-m-toluidine (EHSPT) and 4-aminoantipyrine (4-AA) in the presence of peroxidase (POD) to form a quinone dye which had maximal absorbance at 556 nm. The rate of the quinine dye formation was inversely proportion to the concentration of lithium in serum samples. The enzymatic coupling reaction scheme is shown below in Table 6.

TABLE 6

| | |
|---|---|
| PAP + $H_2O$ $\xrightarrow{\text{Phosphatase}}$ AMP + Pi |
| AMP $\xrightarrow{\text{5'-Nucleotidase/ADA deaminase/PNP}}$ Hypoxanthine + Pi + $NH_3$ + R-1-P |
| Hypoxanthine + $2H_2O$ + $2O_2$ $\xrightarrow{\text{Xanthine Oxidase}}$ Uric Acid + $2H_2O_2$ |
| $H_2O_2$ + 4-AA + EHSPT $\xrightarrow{\text{Peroxidase}}$ $4H_2O$ + Quinone dye ($\lambda$ max 556 nm) |

PAP: 3'-phophoadenosine 5'-phosphate (adenosine 3',5'-bisphosphate)
AMP: Adenosine-5'-phosphate
PNP: Purine Nucleoside Phosphorylase
4-AA: 4-Aminoantipyrine
EHSPT: N-Ethyl-N-(2-Hydroxy-3-Sulfopropyl)-m-Toluidine Key Assay Characteristics. The lithium enzymatic assay was a two reagent (R1 and R2) based kinetic assay system. The results were obtained in 10 min by measuring absorbance at 550 nm. No off line pretreatment was needed. The assay had a wide measuring range from 0 to 3 mmol/L. The assay offered excellent precision as shown in Table 7 below:

TABLE 7

| | 1 mM $Li^+$ | 2 mM $Li^+$ |
|---|---|---|
| Intra-assay | CV % = 3.5% | CV % = 4.5% |
| Inter-assay | CV % = 4.8% | CV % = 4.2% |

Reagent Preparation. One vial of Reagent 1 (R1) was reconstituted with 25 ml distilled water. The reagent was mixed gently by inversion and then allowed to stand for a minimum of 10 min in ice bath before use. The reconstituted R1 solution was stable for 1 week at 2-8° C. One vial of Reagent 2 (R2) was reconstituted with 12.5 ml of distilled water. The reagent was mixed gently by inversion and then allowed to stand for a minimum of 10 min in ice bath before use. The reconstituted R2 solution was stable for 1 week at 2-8° C.

TABLE 8

Reagents

Reagent 1 Buffer/enzyme/substrates
   Enzyme/substrate lyophilized powder containing
   Good's buffer, PAP, $MgCl_2$, 4-AA, Enzymes and stabilizers
Reagent 2 Buffer/protein/substrate
   Enzyme/substrate lyophilized powder containing
   Good's buffer, enzymes, $MgCl_2$, and stabilizers
Low lithium Serum Standard
Med. lithium Serum Standard
High lithium Serum Standard Normal Values. Typically, the desirable serum lithium levels are 0.6 to 1.2 mEq/l.

Test Samples. The test samples were serum or plasma treated with heparin. Plasma containing EDTA-Na should not be used.

Assay Procedure.
1. Reconstituted R1 and R2 reagents as described in Reagent Preparation section and kept the reconstituted R1 and R2 reagents on ice bath.
2. In a cuvette, mixed 180 μL of Reagent R1 and 5 μL of serum sample and incubated at 37° C. for 1 minute and then added 85 μL of Reagent 2.
3. Read absorbance (550 nm) at 6 minutes as $A_1$. Incubated for 3 more minutes and read the absorbance at 9 minute as $A_2$.
4. Calculated $\Delta A = A_2 - A_1$

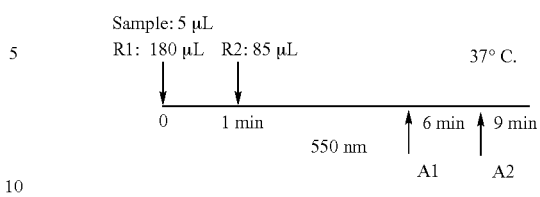

Calibration and Quality Control. The assay was calibrated daily using the enclosed low and high lithium standards. The calibration curve was constructed by plotting the $\Delta A$ values of the standards against the corresponding lithium concentrations. The lithium concentration of the sample was read from the calibration curve. The assay should be calibrated daily.

Interference. The assay was not interfered by the following substances at indicated concentrations: $Na^+$ 200 mM, $NH_4^+$ 0.5 mM, $Ca^{2+}$ 4.0 mM, $Mg^{2+}$ 2.0 mM, ascorbic acid 5.0 mM, 0.25 mM $Zn^{2+}$, 0.25 mM $Fe^{3+}$, 0.25 mM $Cu^{2+}$, 10 mM $K^+$, and billirubin 45 mg/dl.

Performance Features. The assay had a linear range from 0.1-3.0 mM. The intra assay % CV was 3.5%, and the inter assay % CV was 4.5%.

References
1. N. Tietz. TEXTBOOK OF CLINICAL CHEMISTRY, p. 1841. W.B. Sauders Company, Philadelphia (1986)
2. L. Heppel and R. Hilmoe. *J. Bio. Chem.* 188, 665-676 (1951)
3. J. Murguia, J. Belles, and R. Serrano. *Science* 267, 232-234 (1995)

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. An isolated chimeric protein having the enzymatic activity of a nucleotidase, which chimeric protein comprises, from N-terminus to C-terminus:

a) a first peptidyl fragment comprising a bacterial leader sequence comprising the amino acid sequence of SEQ ID NO:1;

b) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and c) a third peptidyl fragment comprising the amino acid sequence of SEQ ID NO:3.

2. The isolated chimeric protein of claim 1, wherein the first and second peptidyl fragments are linked via a cleavable linkage.

3. The isolated chimeric protein of claim 1, which further comprises, at its C-terminus a fourth peptidyl fragment comprising a peptide tag.

4. The isolated chimeric protein of claim 3, wherein the peptide tag is selected from the group consisting of FLAG, HA HA1, c-Myc, 6-His, AU1, EE, T7, 4A6, ε, B, gE, and Ty1 tag.

5. An isolated chimeric protein which comprises the amino acid sequence set forth in SEQ ID NO:4

```
(mggsgddddlalALERELLVATQAVRKASLLTKRIQSEVISHKDSTTITKNDNSPVTTG
DYAAQTIIINAIKSNFPDDKVVGEESSSGLSDAFVSGILNEIKANDEVYNKNYKKD
DFLFTNDQFPLKSLEDVRQIIDFGNYEGGRKGRFWCLDPIDGTKGFLRGEQFAVCL
ALIVDGVVQLGCIGCPNLVLSSYGAQDLKGHESFGYIFRAVRGLGAFYSPSSDAES
WTKIHVRHLKDTKDMITLEGVEKGHSSHDEQTAIKNKLNISKSLHLDSQAKYCLL
ALGLADVYLRLPIKLSYQEKIWDHAAGNVIVHEAGGIHTDAMEDVPLDFGNGRT
LATKGVIASSGPRELHDLVVSTSCDVIQSRNAkgeleglpipnpllrtghhhhhh).
```

6. A method for assaying for sodium ions in a sample, which method comprises:
 a) contacting the sample with a chimeric protein comprising, from N-terminus to C-terminus:
  (i) a first peptidyl fragment comprising a bacterial leader sequence comprising the amino acid sequence of SEQ ID NO:1;
  (ii) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and
  (iii) a third peptidyl fragment comprising the amino acid sequence of SEQ ID NO:3;
  wherein the chimeric protein comprises a sodium-sensitive 3'(2'),5'-bisphosphate nucleotidase, wherein the nucleotidase consumes adenosine 3',5'-bisphosphate (PAP) and forms AMP and P$_i$; and
 b) assessing the consumption of PAP or the formation of AMP or P$_i$ in step a) to determine the presence or amount of sodium ions in the sample.

7. The method of claim 6, wherein the sample is a biological sample.

8. The method of claim 7, wherein the biological sample is a blood sample.

9. The method of claim 8, wherein the blood sample is a plasma, serum, red blood cell, or whole blood sample.

10. The method of claim 6, wherein the amount of AMP formed is inversely related to the amount of sodium ions in the sample.

11. The method of claim 6, which is used in prognosis or diagnosis of a disease or disorder.

12. A method for assaying for sodium ions in a sample, which method comprises:
 a) contacting the sample with a first composition comprising adenosine 3',5'-bisphosphate (PAP);
 b) contacting the sample with a second composition comprising a chimeric protein comprising, from N-terminus to C-terminus:
  (i) a first peptidyl fragment comprising a bacterial leader sequence comprising the amino acid sequence of SEQ ID NO:1;
  (ii) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and
  (iii) a third peptidyl fragment comprising the amino acid sequence of SEQ ID NO:3;
  wherein the chimeric protein comprises a sodium-sensitive 3'(2'),5'-bisphosphate nucleotidase; and
 c) assessing the production of AMP to determine the presence or amount of sodium ions in the sample.

13. The method of claim 12, wherein the sample is a biological sample.

14. The method of claim 13, wherein the biological sample is a blood sample.

15. The method of claim 14, wherein the blood sample is a plasma, serum, red blood cell, or whole blood sample.

16. The method of claim 12, wherein the first composition further comprises 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, and the second composition further comprises adenosine deaminase, 5'-nucleotidase, and MgCl$_2$.

17. A kit for assaying for sodium ions in a sample, which kit comprises:
 a) a first composition comprising a chimeric protein comprising, from N-terminus to C-terminus:
  (i) a first peptidyl fragment comprising a bacterial leader sequence comprising the amino acid sequence of SEQ ID NO:1;
  (ii) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and
  (iii) a third peptidyl fragment comprising the amino acid sequence of SEQ ID NO:3;
  wherein the chimeric protein comprises a sodium-sensitive 3'(2'),5'-bisphosphate nucleotidase that consumes adenosine 3',5'-bisphosphate and forms AMP and P$_i$; and
 b) means for assessing the product formed or the substrate consumed by the nucleotidase to determine the presence or amount of the sodium ions in the sample.

18. The kit of claim 17, wherein the first composition further comprises adenosine deaminase, 5'-nucleotidase and MgCl$_2$.

19. The kit of claim 17, further comprising a second composition comprising 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, wherein the reaction of 4-AA and EHSPT in the presence of peroxidase is the means for assessing the product formed.

20. The kit of claim 17, which further comprises a low sodium serum standard and a high sodium serum standard.

21. A method for assaying for lithium ions in a sample, which method comprises:
    a) contacting the sample with a chimeric protein comprising, from N-terminus to C-terminus:
        (i) a first peptidyl fragment comprising a bacterial leader sequence comprising the amino acid sequence of SEQ ID NO:1;
        (ii) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and
        (iii) a third peptidyl fragment comprising the amino acid sequence of SEQ ID NO:3;
        wherein the chimeric protein comprises a lithium-sensitive 3'(2'),5'-bisphosphate nucleotidase, wherein the nucleotidase consumes adenosine 3',5'-bisphosphate (PAP) and forms AMP and $P_i$; and
    b) assessing the amount of PAP consumed or AMP or Pi formed in step (a) to determine the presence or absence of lithium ions in the sample.

22. The method of claim 21 further comprising first contacting the sample with a sodium blocking agent.

23. The method of claim 22, wherein the sodium blocking agent is 4, 7, 13, 16, 21-pentaoxa-1,10-diazabicyclo[8.8.5]-tricosane.

24. The method of claim 22, wherein the sample is a biological sample.

25. The method of claim 24, wherein the biological sample is a blood sample.

26. The method of claim 25, wherein the blood sample is a plasma, serum, red blood cell, or whole blood sample.

27. The method of claim 22, wherein the amount of AMP formed is inversely correlated to the amount of lithium ions in the sample.

28. The method of claim 22, which is used in prognosis or diagnosis of a disease or disorder.

29. A method for assaying for lithium ions in a sample, which method comprises:
    a) contacting the sample with a first composition comprising adenosine 3',5'-bisphosphate (PAP);
    b) contacting the sample with a second composition comprising a chimeric protein comprising, from N-terminus to C-terminus:
        (i) a first peptidyl fragment comprising a bacterial leader sequence comprising the amino acid sequence of SEQ ID NO:1;
        (ii) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and
        (iii) a third peptidyl fragment comprising the amino acid sequence of SEQ ID NO:3;
        wherein the chimeric protein comprises a lithium-sensitive 3'(2'),5'-bisphosphate nucleotidase; and
    c) assessing the production of a detectable product to determine the presence or absence of lithium ions in the sample.

30. The method of claim 29 further comprising first contacting the sample with a sodium blocking agent.

31. The method of claim 30, wherein the sodium blocking agent is 4, 7, 13, 16, 21-pentaoxa-1,10-diazabicyclo[8.8.5]-tricosane.

32. The method of claim 29, wherein the sample is a biological sample.

33. The method of claim 32, wherein the biological sample is a blood sample.

34. The method of claim 33, wherein the blood sample is a plasma, serum, red blood cell, or whole blood sample.

35. The method of claim 29, wherein the first composition further comprises 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, and the second composition further comprises adenosine deaminase, 5'-nucleotidase, and $MgCl_2$.

36. A kit for assaying for lithium ion in a sample, which kit comprises:
    a) a first composition comprising a chimeric protein comprising, from N-terminus to C-terminus:
        (i) a first peptidyl fragment comprising a bacterial leader sequence comprising the amino acid sequence of SEQ ID NO:1;
        (ii) a second peptidyl fragment comprising the amino acid sequence of SEQ ID NO:2 or comprising the amino acid sequence of SEQ ID NO:2 having a single conservative amino acid substitution, wherein the substituted peptidyl fragment retains at least 90% of the 3'(2'),5'-bisphosphonate activity of SEQ ID NO:2; and
        (iii) a third peptidyl fragment comprising the amino acid sequence of SEQ ID NO:3;
        wherein the chimeric protein comprises a lithium-sensitive 3'(2'),5'-bisphosphate nucleotidase; and
    b) a means for assessing the adenosine 3',5'-bisphosphate consumed or the AMP or Pi formed by the 3'(2'),5'-bisphosphate nucleotidase to determine the presence or amount of said lithium ions in the sample.

37. The kit of claim 36 further comprising a sodium blocking agent.

38. The kit of claim 36, wherein the first composition further comprises adenosine deaminase, 5'-nucleotidase and $MgCl_2$.

39. The kit of claim 36, further comprising a second composition comprising 4-aminoantipyrine (4-AA), N-ethyl-N-(2-hydroxy-3-sulfopropyl)-3-m-toluidine (EHSPT), purine nucleoside phosphorylase, xanthine oxidase, and peroxidase, wherein the reaction of 4-AA and EHSPT in the presence of peroxidase is the means for assessing the product formed.

40. The kit of claim 36, which further comprises a low lithium serum standard, a medium lithium sodium standard, and a high lithium serum standard.

* * * * *

SEQUENCE LISTING

<160> NUMBER OF SEQ ID NOS: 18

<210> SEQ ID NO 1
<211> LENGTH: 12
<212> TYPE: PRT
<213> ORGANISM: Artificial Sequence
<220> FEATURE:
<223> OTHER INFORMATION: Chimeric protein

<400> SEQUENCE: 1

Met Gly Gly Ser Gly Asp Asp Asp Asp Leu Ala Leu
1               5                   10

<210> SEQ ID NO 2
<211> LENGTH: 356
<212> TYPE: PRT
<213> ORGANISM: Artificial Sequence
<220> FEATURE:
<223> OTHER INFORMATION: Chimeric protein

<400> SEQUENCE: 2

Ala Leu Glu Arg Glu Leu Leu Val Ala Thr Gln Ala Val Arg Lys Ala
1               5                   10                  15

Ser Leu Leu Thr Lys Arg Ile Gln Ser Glu Val Ile Ser His Lys Asp
            20                  25                  30

```
Ser Thr Thr Ile Thr Lys Asn Asp Asn Ser Pro Val Thr Thr Gly Asp
        35                  40                  45

Tyr Ala Ala Gln Thr Ile Ile Ile Asn Ala Ile Lys Ser Asn Phe Pro
    50                  55                  60

Asp Asp Lys Val Val Gly Glu Glu Ser Ser Gly Leu Ser Asp Ala
65                  70                  75                  80

Phe Val Ser Gly Ile Leu Asn Glu Ile Lys Ala Asn Asp Glu Val Tyr
                85                  90                  95

Asn Lys Asn Tyr Lys Lys Asp Asp Phe Leu Phe Thr Asn Asp Gln Phe
                100                 105                 110

Pro Leu Lys Ser Leu Glu Asp Val Arg Gln Ile Ile Asp Phe Gly Asn
            115                 120                 125

Tyr Glu Gly Gly Arg Lys Gly Arg Phe Trp Cys Leu Asp Pro Ile Asp
        130                 135                 140

Gly Thr Lys Gly Phe Leu Arg Gly Glu Gln Phe Ala Val Cys Leu Ala
145                 150                 155                 160

Leu Ile Val Asp Gly Val Val Gln Leu Gly Cys Ile Gly Cys Pro Asn
                165                 170                 175

Leu Val Leu Ser Ser Tyr Gly Ala Gln Asp Leu Lys Gly His Glu Ser
                180                 185                 190

Phe Gly Tyr Ile Phe Arg Ala Val Arg Gly Leu Gly Ala Phe Tyr Ser
            195                 200                 205

Pro Ser Ser Asp Ala Glu Ser Trp Thr Lys Ile His Val Arg His Leu
        210                 215                 220

Lys Asp Thr Lys Asp Met Ile Thr Leu Glu Gly Val Glu Lys Gly His
225                 230                 235                 240

Ser Ser His Asp Glu Gln Thr Ala Ile Lys Asn Lys Leu Asn Ile Ser
                245                 250                 255

Lys Ser Leu His Leu Asp Ser Gln Ala Lys Tyr Cys Leu Leu Ala Leu
                260                 265                 270

Gly Leu Ala Asp Val Tyr Leu Arg Leu Pro Ile Lys Leu Ser Tyr Gln
            275                 280                 285

Glu Lys Ile Trp Asp His Ala Ala Gly Asn Val Ile Val His Glu Ala
        290                 295                 300

Gly Gly Ile His Thr Asp Ala Met Glu Asp Val Pro Leu Asp Phe Gly
305                 310                 315                 320

Asn Gly Arg Thr Leu Ala Thr Lys Gly Val Ile Ala Ser Ser Gly Pro
                325                 330                 335

Arg Glu Leu His Asp Leu Val Val Ser Thr Ser Cys Asp Val Ile Gln
            340                 345                 350

Ser Arg Asn Ala
        355

<210> SEQ ID NO 3
<211> LENGTH: 17
<212> TYPE: PRT
<213> ORGANISM: Artificial Sequence
<220> FEATURE:
<223> OTHER INFORMATION: Chimeric protein

<400> SEQUENCE: 3

Lys Gly Glu Leu Glu Gly Leu Pro Ile Pro Asn Pro Leu Leu Arg Thr
1               5                   10                  15

Gly
```

<210> SEQ ID NO 4
<211> LENGTH: 391
<212> TYPE: PRT
<213> ORGANISM: Artificial Sequence
<220> FEATURE:
<223> OTHER INFORMATION: Chimeric protein

<400> SEQUENCE: 4

Met Gly Gly Ser Gly Asp Asp Asp Leu Ala Leu Ala Leu Glu Arg
1               5                   10                  15

Glu Leu Leu Val Ala Thr Gln Ala Val Arg Lys Ala Ser Leu Leu Thr
            20                  25                  30

Lys Arg Ile Gln Ser Glu Val Ile Ser His Lys Asp Ser Thr Thr Ile
        35                  40                  45

Thr Lys Asn Asp Asn Ser Pro Val Thr Thr Gly Asp Tyr Ala Ala Gln
    50                  55                  60

Thr Ile Ile Ile Asn Ala Ile Lys Ser Asn Phe Pro Asp Asp Lys Val
65                  70                  75                  80

Val Gly Glu Glu Ser Ser Gly Leu Ser Asp Ala Phe Val Ser Gly
                85                  90                  95

Ile Leu Asn Glu Ile Lys Ala Asn Asp Glu Val Tyr Asn Lys Asn Tyr
                100                 105                 110

Lys Lys Asp Asp Phe Leu Phe Thr Asn Asp Gln Phe Pro Leu Lys Ser
            115                 120                 125

Leu Glu Asp Val Arg Gln Ile Ile Asp Phe Gly Asn Tyr Glu Gly Gly
        130                 135                 140

Arg Lys Gly Arg Phe Trp Cys Leu Asp Pro Ile Asp Gly Thr Lys Gly
145                 150                 155                 160

Phe Leu Arg Gly Glu Gln Phe Ala Val Cys Leu Ala Leu Ile Val Asp
                165                 170                 175

Gly Val Val Gln Leu Gly Cys Ile Gly Cys Pro Asn Leu Val Leu Ser
                180                 185                 190

Ser Tyr Gly Ala Gln Asp Leu Lys Gly His Glu Ser Phe Gly Tyr Ile
            195                 200                 205

Phe Arg Ala Val Arg Gly Leu Gly Ala Phe Tyr Ser Pro Ser Ser Asp
        210                 215                 220

Ala Glu Ser Trp Thr Lys Ile His Val Arg His Leu Lys Asp Thr Lys
225                 230                 235                 240

Asp Met Ile Thr Leu Glu Gly Val Glu Lys Gly His Ser Ser His Asp
                245                 250                 255

Glu Gln Thr Ala Ile Lys Asn Lys Leu Asn Ile Ser Lys Ser Leu His
            260                 265                 270

Leu Asp Ser Gln Ala Lys Tyr Cys Leu Leu Ala Leu Gly Leu Ala Asp
        275                 280                 285

Val Tyr Leu Arg Leu Pro Ile Lys Leu Ser Tyr Gln Glu Lys Ile Trp
    290                 295                 300

Asp His Ala Ala Gly Asn Val Ile Val His Glu Ala Gly Gly Ile His
305                 310                 315                 320

Thr Asp Ala Met Glu Asp Val Pro Leu Asp Phe Gly Asn Gly Arg Thr
                325                 330                 335

Leu Ala Thr Lys Gly Val Ile Ala Ser Ser Gly Pro Arg Glu Leu His
            340                 345                 350

Asp Leu Val Val Ser Thr Ser Cys Asp Val Ile Gln Ser Arg Asn Ala
        355                 360                 365

```
Lys Gly Glu Leu Glu Gly Leu Pro Ile Pro Asn Pro Leu Leu Arg Thr
370                 375                 380

Gly His His His His His
385                 390

<210> SEQ ID NO 5
<211> LENGTH: 1176
<212> TYPE: DNA
<213> ORGANISM: Artificial Sequence
<220> FEATURE:
<223> OTHER INFORMATION: Nucleotide sequence encoding a chimeric protein

<400> SEQUENCE: 5
atgggcggat ccggtgatga cgatgacctc gcccttgcat tggaaagaga attattggtt      60
gcaactcaag ctgtacgaaa ggcgtcttta ttgactaaga gaattcaatc tgaagtgatt     120
tctcacaagg actccactac tattaccaag aatgataatt ctccagtaac cacaggtgat     180
tatgctgcac aaacgatcat cataaatgct atcaagagca attttcctga tgataaggta     240
gttggtgaag aatcctcatc aggattgagc gacgcattcg tctcaggaat tttaaacgaa     300
ataaaagcca atgacgaagt ttataacaag aattataaaa aggatgattt tctgtttaca     360
aacgatcagt ttccgctaaa atctttggag gacgtcaggc aaatcatcga tttcggcaat     420
tacgaaggtg gtagaaaagg aagattttgg tgtttggatc ctattgacgg aaccaagggg     480 ttttaagag gtgaacagtt tgcagtatgt ctggccttaa ttgtggacgg tgttgttcag     540
cttggttgta ttggatgccc caacttagtt ttaagttctt atggggccca agatttgaaa     600
ggccatgagt catttggtta tatctttcgt gctgttagag gttaggtgc cttctattct     660 ccatcttcag atgcagagtc atggaccaaa atccacgtta gacacttaaa agacactaaa     720
gacatgatta ctttagaggg agttgaaaag ggacactcct ctcatgatga acaaactgct     780
atcaaaaaca aactaaatat atccaaatct ttgcacttgg attctcaagc caagtactgt     840 tgttagcat tgggcttagc agacgtatat ttacgtctgc ctatcaaact ttcttaccaa     900
gaaaagatct gggaccatgc tgcaggcaac gttattgtcc atgaagctgg aggtatccat     960
acagatgcca tggaagatgt tcctctagac ttcggtaacg gtagaacgct agctacgaag    1020
ggagttatag cgtcaagtgg cccacgcgag ttacatgact tggtggtgtc tacatcatgc    1080
gatgtcattc agtcaagaaa cgccaagggc gagcttgaag gtttgcctat ccctaaccct    1140
ctcctccgta ccggtcatca tcaccatcac cattga                             1176

<210> SEQ ID NO 6
<211> LENGTH: 7
<212> TYPE: PRT
<213> ORGANISM: Artificial Sequence
<220> FEATURE:
<223> OTHER INFORMATION: Exemplary epitope tag

<400> SEQUENCE: 6

Asp Tyr Lys Asp Asp Asp Lys
 1               5

<210> SEQ ID NO 7
<211> LENGTH: 9
<212> TYPE: PRT
<213> ORGANISM: Artificial Sequence
<220> FEATURE:
<223> OTHER INFORMATION: Exemplary epitope tag
```

```
<400> SEQUENCE: 7

Tyr Pro Tyr Asp Val Pro Asp Tyr Ala
1               5

<210> SEQ ID NO 8
<211> LENGTH: 11
<212> TYPE: PRT
<213> ORGANISM: Artificial Sequence
<220> FEATURE:
<223> OTHER INFORMATION: Exemplary epitope tag

<400> SEQUENCE: 8

Cys Gln Asp Leu Pro Gly Asn Asp Asn Ser Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Exemplary epitope tag

<400> SEQUENCE: 9

Glu Gln Lys Leu Ile Ser Glu Glu Asp Leu
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Exemplary epitope tag

<400> SEQUENCE: 10

His His His His His His
1               5

<210> SEQ ID NO 11
<211> LENGTH: 6
<212> TYPE: PRT
<213> ORGANISM: Artificial Sequence
<220> FEATURE:
<223> OTHER INFORMATION: Exemplary epitope tag

<400> SEQUENCE: 11

Asp Thr Tyr Arg Tyr Ile
1               5

<210> SEQ ID NO 12
<211> LENGTH: 6
<212> TYPE: PRT
<213> ORGANISM: Artificial Sequence
<220> FEATURE:
<223> OTHER INFORMATION: Exemplary epitope tag

<400> SEQUENCE: 12

Glu Tyr Met Pro Met Glu
1               5

<210> SEQ ID NO 13
<211> LENGTH: 11
<212> TYPE: PRT
<213> ORGANISM: Artificial Sequence
<220> FEATURE:
<223> OTHER INFORMATION: Exemplary epitope tag
```

```
<400> SEQUENCE: 13

Ala Ser Met Thr Gly Gly Gln Gln Met Gly Arg
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Exemplary epitope tag

<400> SEQUENCE: 14

Ser Phe Pro Gln Phe Lys Pro Gln Glu Ile
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Exemplary epitope tag

<400> SEQUENCE: 15

Lys Gly Phe Ser Tyr Phe Gly Glu Asp Leu Met Pro
 1               5                  10

<210> SEQ ID NO 16
<211> LENGTH: 6
<212> TYPE: PRT
<213> ORGANISM: Artificial Sequence
<220> FEATURE:
<223> OTHER INFORMATION: Exemplary epitope tag

<400> SEQUENCE: 16

Gln Tyr Pro Ala Leu Thr
 1               5

<210> SEQ ID NO 17
<211> LENGTH: 11
<212> TYPE: PRT
<213> ORGANISM: Artificial Sequence
<220> FEATURE:
<223> OTHER INFORMATION: Exemplary epitope tag

<400> SEQUENCE: 17

Gln Arg Gln Tyr Gly Asp Val Phe Lys Gly Asp
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Exemplary epitope tag

<400> SEQUENCE: 18

Glu Val His Thr Asn Gln Asp Pro Leu Asp
 1               5                  10
```